(12) United States Patent
Yoshida et al.

(10) Patent No.: US 7,662,778 B2
(45) Date of Patent: Feb. 16, 2010

(54) HISTONE DEACETYLASE INHIBITOR AND PROCESS FOR PRODUCING THE SAME

(75) Inventors: Minoru Yoshida, Saitama (JP); Norikazu Nishino, Fukuoka (JP)

(73) Assignee: Riken, Wako-shi, Saitama (JP)

(*) Notice: Subject to any disclaimer, the term of this patent is extended or adjusted under 35 U.S.C. 154(b) by 361 days.

(21) Appl. No.: 10/561,298

(22) PCT Filed: Jun. 18, 2004

(86) PCT No.: PCT/JP2004/008924
§ 371 (c)(1), (2), (4) Date: Jun. 7, 2006

(87) PCT Pub. No.: WO2004/113366
PCT Pub. Date: Dec. 29, 2004

(65) Prior Publication Data
US 2007/0185071 A1    Aug. 9, 2007

(30) Foreign Application Priority Data
Jun. 20, 2003   (JP)   ............................. 2003-177298

(51) Int. Cl.
*A61K 38/00* (2006.01)
(52) U.S. Cl. ........................................................ 514/11
(58) Field of Classification Search ........................ None
See application file for complete search history.

(56) References Cited

U.S. PATENT DOCUMENTS

| | | | |
|---|---|---|---|
| 5,922,837 A | 7/1999 | Meinke et al. | |
| 6,399,568 B1 | 6/2002 | Nishino et al. | |
| 7,488,712 B2 | 2/2009 | Yoshida | |
| 2002/0120099 A1 | 8/2002 | Nishino et al. | |
| 2003/0078369 A1* | 4/2003 | Meinke et al. | 530/317 |

FOREIGN PATENT DOCUMENTS

| | | |
|---|---|---|
| CA | 2 317 003 | 8/2000 |
| EP | 1 010 705 | 6/2000 |
| EP | 1 174 438 | 1/2002 |
| JP | 11-130795 | 5/1999 |
| JP | EP 1010705 * | 6/2000 |
| JP | 2000-256397 | 9/2000 |
| JP | 2001-316283 | 11/2001 |
| JP | 2002-527449 | 8/2002 |
| JP | 2003-505417 | 2/2003 |
| WO | WO 00/21979 | 4/2000 |
| WO | WO 00/52033 | 9/2000 |
| WO | WO 01/07042 | 2/2001 |
| WO | WO 03/057722 | 7/2003 |
| WO | WO 03/070754 | 8/2003 |

OTHER PUBLICATIONS

Saito A, "A synthetic inhibitor of histone deacetylase, MS-27-275, with marked in vivo antitumor activity against human tumors," Proc Natl Acad Sci U S A. Apr. 13, 1999;96(8):4592-7.*

Bernhard et al., "Interaction between dexamethasone and butyrate in apoptosis induction: non-additive in thymocytes and synergistic in a T cell-derived leukemia cell line," *Cell Death Diff.*, 1999, 6:609-617.

Boivin et al., "Antineoplastic action of 5-aza-2'-deoxycytidine and phenylbutyrate on human lung carcinoma cells," *Anti-Cancer Drugs*, 2002, 13:869-874.

Cameron et al., "Synergy of demethylation and histone deacetylase inhibition in the re-expression of genes silenced in cancer," *Nature Genet.*, 1999, 21:103-107.

Chen et al., "Reactivation of silenced, virally transduced genes by inhibitors of histone deacetylase," *Proc. Natl. Acad. Sci. USA*, 1997, 94:5798-5803.

Coffey et al., "The Histone Deacetylase Inhibitor, CBHA, Inhibits Growth of Human Neuroblastoma Xenografts in Vivo, Alone and Synergistically with *All-Trans* Retinoic Acid," *Cancer Res.*, 2001, 61:3591-3594.

Colletti et al., "Design and synthesis of histone deacetylase inhibitors: the development of apicidin transition state analogs," *Tetrahedron Lett.*, 2000, 41:7837-7841.

Colletti et al., "Broad Spectrum Antiprotozoal Agents that Inhibit Histone Deacetylase: Structure-Activity Relationships of Apicidin. Part 2," *Bioorg. Med. Chem. Lett.*, 2001, 11:113-117.

Darkin-Rattray et al., "Apicidin: A novel antiprotozoal agent that inhibits parasite histone deacetylase," *Proc. Natl. Acad. Sci. USA*, 1996, 93:13143-13147.

De Schepper et al., "Inhibition of Histone Deacetylases by Chlamydocin Induces Apoptosis and Proteasome-Mediated Degradation of Survivin," *J. Pharmacol. Exp. Ther.*, 2003, 304(2):881-888.

Dhordain et al., "Corepressor SMRT binds the BTB/POZ repressing domain of the LAZ3/BCL6 oncoprotein," *Proc. Natl. Acad. Sci. USA*, 1997, 94:10762-10767.

Dion et al., "Amplification of Recombinant Adenoviral Transgene Products Occurs by Inhibition of Histone Deacetylase," *Virology*, 1997, 231:201-209.

Ferrara et al., "Histone Deacetylase-targeted Treatment Restores Retinoic Acid Signaling and Differentiation in Acute Myeloid Leukemia," *Cancer Res.*, 2001, 61:2-7.

Finnin et al., "Structures of a histone deacetylase homologue bound to the TSA and SAHA inhibitors," *Nature*, 1999, 401:188-193.

(Continued)

*Primary Examiner*—Cecilia Tsang
*Assistant Examiner*—Thomas S Heard
(74) *Attorney, Agent, or Firm*—Fish & Richardson P.C.

(57) ABSTRACT

HDAC inhibitor of the general formula (1) exhibits strong inhibitory activity against various subtype HDACs. The compound is useful as a medicinal agent for the treatment or prevention of HDAC 1, 4 and 6-related diseases. There is further provided a process for producing the compound which is capable of readily synthesizing various types of compounds and is promising in the contribution to the development of HDAC inhibitor having novel properties, etc.

9 Claims, 5 Drawing Sheets

OTHER PUBLICATIONS

Fischle et al., "A New Family of Human Histone Deacetylases Related to *Saccharomyces cerevisiae* HDA1p," *J. Biol. Chem.*, 1999, 274(17):11713-11720.

Frey et al., "Trifluoromethyl Ketones as Inhibitors of Histone Deacetylase," *Bioorg. Med. Chem. Lett.*, 2002, 12:3443-3447.

Furumai et al., "Potent histone deacetylase inhibitors built from trichostatin A and cyclic tetrapeptide antibiotics including trapoxin," *Proc. Natl. Acad. Sci. USA*, 2001, 98(1):87-92.

Furumai et al., "FK228 (Depsipeptide) as a Natural Prodrug That Inhibits Class I Histone Deacetylases," *Cancer Res.*, 2002, 62:4916-4921.

Göttlicher et al., "Valproic acid defines a novel class of HDAC inhibitors inducing differentiation of transformed cells," *EMBO J.*, 2001, 20(24):6969-6978.

Grignani et al., "Fusion proteins of the retinoic acid receptor-α recruit histone deacetylase in promyelocytic leukaemia," *Nature*, 1998, 391:815-818.

He et al., "Distinct interactions of PML-RARα and PLZF-RARα with co-repressors determine differential responses to RA in APL," *Nature Genet.*, 1998, 18:126-135.

Hoshi et al., "Activation of a $Ca^{2+}$-inhibitable Protein Kinase That Phosphorylates Microtubule—associated Protein 2 in Vitro by Growth Factors, Phorbol Esters, and Serum in Quiescent Cultured Human Fibroblasts," *J. Biol. Chem.*, 1988, 263(11):5396-5401.

Hoshikawa et al., "Expression of Differentiation-related Markers in Teratocarcinoma Cells via Histone Hyperacetylation by Trichostatin A," *Agric. Biol. Chem.*, 1991, 55(6):1491-1495.

Hubbert et al., "HDAC6 is a microtubule-associated deacetylase," *Nature*, 2002, 417:455-458.

Inokoshi et al., "Neuronal Differentiation of Neuro 2a Cells by Inhibitors of Cell Cycle Progression, Trichostatin A and Butyrolactone I," *Biochem. Biophys. Res. Commun.*, 1999, 256(2):372-376.

Ito et al., "p300/CBP-mediated p53 acetylation is commonly induced by p53-activating agents and inhibited by MDM2," *EMBO J.*, 2001, 20(6):1331-1340.

Jose et al., "Toward an HDAC6 inhibitor: synthesis and conformational analysis of cyclic hexapeptide hydroxamic acid designed from α-tubulin sequence," *Bioorg. Med. Chem.*, 2004, 12:1351-1356.

Juan et al., "Histone Deacetylases Specifically Down-regulate p53-dependent Gene Activation," *J. Biol. Chem.*, 2000, 275(27):20436-20443.

Kim et al., "Histone deacetylases induce angiogenesis by negative regulation of tumor suppressor genes," *Nature Med.*, 2001, 7(4):437-443.

Kim et al., "Oxamflatin is a novel antitumor compound that inhibits mammalian histone deacetylase," *Oncogene*, 1999, 18:2461-2470.

Komatsu et al., "Cyclic Hydroxamic-acid-containing Peptide 31, a Potent Synthetic Histone Deacetylase Inhibitor with Antitumor Activity," *Cancer Res.*, 2001, 61:4459-4466.

Kwon et al., "Histone deacetylase inhibitor FK228 inhibits tumor angiogenesis," *Int. J. Cancer*, 2002, 97:290-296.

Li et al., "Causal Relationship between the Loss of *RUNX3* Expression and Gastric Cancer," *Cell*, 2002, 109:113-124.

Lin et al., "Role of the histone deacetylase complex in acute promyelocytic leukaemia," *Nature*, 1998, 391:811-814.

Liu et al., "Histone Deacetylase Inhibitor Up-Regulates RECK to Inhibit MMP-2 Activation and Cancer Cell Invasion," *Cancer Res.*, 2003, 63:3069-3072.

Marks et al., "Histone Deacetylase Inhibitors: Inducers of Differentiation or Apoptosis of Transformed Cells," *J. Natl. Cancer Inst.*, 2000, 92(15):1210-1216.

Matsuyama et al., "In vivo destabilization of dynamic microtubules by HDAC6-mediated deacetylation," *EMBO J.*, 2002, 21(24):6820-6831.

McCampbell et al., "Histone deacetylase inhibitors reduce polyglutamine toxicity," *Proc. Natl. Acad. Sci. USA*, 2001, 98(26):15179-15184.

McKinsey et al., "Signal-dependent nuclear export of a histone deacetylase regulates muscle differentiation," *Nature*, 2000, 408:106-111.

Meinke et al., "Synthesis of side chain modified apicidin derivatives: potent mechanism-based histone deacetylase inhibitors," *Tetrahedron Lett.*, 2000, 41:7831-7835.

Minucci et al., "A histone deacetylase inhibitor potentiates retinoid receptor action in embryonal carcinoma cells," *Proc. Natl. Acad. Sci. USA*, 1997, 94:11295-11300.

Mori et al., "FR235222, a Fungal Metabolite, is a Novel Immunosuppressant that Inhibits Mammalian Histone Deacetylase (HDAC). 1. Taxonomy, Fermentation, Isolation and Biological Activities," *J. Antibiot.*, 2003, 56(2):72-79.

Munster et al., "The Histone Deacetylase Inhibitor Suberoylanilide Hydroxamic Acid Induces Differentiation of Human Breast Cancer Cells," *Cancer Res.*, 2001, 61:8492-8497.

Nakajima et al., "FR901228, a Potent Antitumor Antibiotic, Is a Novel Histone Deacetylase Inhibitor," *Exp. Cell Res.*, 1998, 241:126-133.

Nan et al., "Transcriptional repression by the methyl-CpG-binding protein MeCP2 involves a histone deacetylase complex," *Nature*, 1998, 393:386-389.

Nishino et al., "Synthesis and histone deacetylase inhibitory activity of cyclic tetrapeptides containing a retrohydroxamate as zinc ligand," *Bioorg. Med. Chem. Lett.*, 2004, 14:2427-2431.

Petti et al., "Complete remission through blast cell differentiation in *PLZF/RARα*-positive acute promyelocytic leukemia: in vitro and in vivo studies," *Blood*, 2002, 100(3):1065-1067.

Primeau et al., "Synergistic antineoplastic action of DNA methylation inhibitor 5-AZA-2'-deoxycytidine and histone deacetylase inhibitor depsipeptide on human breast carcinoma cells," *Int. J. Cancer*, 2003, 103:177-184.

Rombouts et al., "Trichostatin A, a Histone Deacetylase Inhibitor, Suppresses Collagen Synthesis and Prevents $TGF-\beta_1$-Induced Fibrogenesis in Skin Fibroblasts," *Exp. Cell. Res.*, 2002, 278:184-197.

Ryu et al., "Histone deacetylase inhibitors prevent oxidative neuronal death independent of expanded polyglutamine repeats via an Sp1-dependent pathway," *Proc. Natl. Acad. Sci. USA*, 2003, 100(7):4281-4286.

Saito et al. "A synthetic inhibitor of histone deacetylase, MS-27-275, with marked in vivo antitumor activity against human tumors," *Proc. Natl. Acad. Sci. USA*, 1999, 96:4592-4597.

Scherer et al., "Studies on the Propagation in Vitro of Poliomyelitis Viruses. IV. Viral Multiplication in a Stable Strain of Human Malignant Epithelial Cells (Strain HeLa) Derived from an Epidermoid Carcinoma of the Cervix," *J. Exp. Med.*, 1953, 97:695-710.

Skov et al., "Histone deacetylase inhibitors: a new class of immunosuppressors targeting a novel signal pathway essential for CD154 expression," *Blood*, 2003, 101(4):1430-1438.

Steffan et al., "Histone deacetylase inhibitors arrest polyglutamine-dependent neurodegeneration in *Drosophila*," *Nature*, 2001, 413:739-743.

Verdel and Khochbin, "Identification of a New Family of Higher Eukaryotic Histone Deacetylases. Coordinate Expression of Differentiation-dependent Dhromatin Modifiers," *J. Biol. Chem.*, 1999, 274(4):2440-2445.

Verdel et al., "Active maintenance of mHDA2/mHDAC6 histone-deacetylase in the cytoplasm," *Curr. Biol.*, 2000, 10:747-749.

Wang et al., "Inhibitors of Histone Deacetylase Relieve ETO-mediated Repression and Induce Differentiation of AML1-ETO Leukemia Cells," *Cancer Res.*, 1999, 59:2766-2769.

Yang et al., "Isolation and Characterization of cDNAs Corresponding to an Additional Member of the Human Histone Deacetylase Gene Family," *J. Biol. Chem.*, 1997, 272(44):28001-28007.

Yoshida et al., "Effects of Trichostatins on Differentiation of Murine Erythroleukemia Cells," *Cancer Res.*, 1987, 47:3688-3691.

Yoshida et al., "Potent and Specific Inhibition of Mammalian Histone Deacetylase Both in Vivo and in Vitro by Trichostatin A," *J. Biol. Chem.*, 1990, 265(28):17174-17179.

Yoshida et al., "Trichostatin A and trapoxin: novel chemical probes for the role of histone acetylation in chromatin structure and function," *BioEssays*, 1995, 17(5):423-430.

Zhang et al., "HDAC-6 interacts with and deacetylates tubulin and microtubules in vivo," *EMBO J.*, 2003, 22(5):1168-1179.

* cited by examiner

Cyl-1

Cyl-2

HISTONE DEACETYLASE INHIBITOR AND PROCESS FOR PRODUCING THE SAME

CROSS-REFERENCE TO RELATED APPLICATIONS

This application is a National Stage application under 35 U.S.C. § 371 and claims benefit under 35 U.S.C. § 119(a) of International Application No. PCT/JP2004/008924, having an International Filing Date of Jun. 18, 2004, which claims the benefit of priority of Japanese Application No. 2003/177298, filed Jun. 20, 2003.

TECHNICAL FIELD

The present invention relates to histone deacetylase (HDAC) inhibitors and methods for producing the same.

BACKGROUND ART

Eukaryotic chromatin structure and gene expression are regulated by histone acetylation by histone acetyltransferase (HAT), and deacetylation by histone deacetylase (HDAC). HDAC inhibitors are already known to induce cancer cell differentiation and apoptosis, and are expected to be useful as antitumor agents (Non-Patent Documents 1-3). In fact, clinical studies have begun in the United States for some HDAC inhibitors (on-Patent Documents 4 and 5) that are effective as antitumor agents in animal experiments.

Tricostatin A (TSA) is well known as a specific HDAC inhibitor (Non-Patent Document 6). In fact, TSA has been known to induce differentiation to leukemia cells, neuronal cells, breast cancer cells, and the like (Non-Patent Documents 7-14). Furthermore, the TSA activities of differentiation induction and apoptosis induction are known to synergistically increase when used in combination with drugs that activate gene expression by mechanisms different from HDAC inhibitors. For example, cancer cell differentiation can be promoted by using HDAC inhibitors in combination with retinoic acids, which activate retinoic acid receptors that serve as nuclear receptors, thereby inducing gene expression relevant to differentiation (Non-Patent Documents 9, 13, 15, and 16). 5-azadeoxycytidine inhibits DNA methylation to reduce expression of tumor suppressor genes in many cancer cells. TSA used in combination with 5-azadeoxycytidine promotes cancer cell apoptosis and restoration of tumor-suppressing gene expression (Non-Patent Documents 17-21).

HDAC inhibitors are expected to act not only as antitumor agents but also as cancer preventives. TSA, SAHA, and the like significantly suppressed the occurrence of breast cancer induced in animal models. Also, investigations carried out using valproic acids indicated that HDAC inhibitors suppress metastasis (Non-Patent Document 14).

In addition to applications as antitumor agents, HDAC inhibitors have other applications, including as therapeutic and ameliorative agents for autoimmune diseases, neurodegenerative diseases such as polyglutamine disease (Non-Patent Documents 22 and 23), skin diseases, and infectious diseases (Non-patent Document 24). HDAC inhibitors are also used to improve efficiency of vector transfer for gene therapy (Non-Patent Document 25), and enhance expression of transferred genes (Non-Patent Document 26). HDAC inhibitors may also have inhibitory effects against angiogenesis (Non-Patent Document 27 and 28).

There are 10 or more subtypes of HDAC, and recently, certain HDAC subtypes have been found to be closely related to cancer. For example, for tumor suppressor gene p53, which plays a very important role in inhibiting cancer development, to express its faction, acetylation of p53 itself is important (Non-Patent Document 29) and HDAC1 and HDAC2 have been found to be involved in inhibiting this function (Non-Patent Document 30). It has also been demonstrated that HDAC4 and the like are recruited via nuclear corepressors by oncogenes, such as PML-RAR and PLZF-RAR, proteins involved in development of acute promyelocytic leukemia (APL) and Bcl-6, involved in the development of lymphoma, and lead to cancer development by inhibiting the expression of a group of genes required for normal differentiation (Non-Patent Documents 31-34). In addition, among tissue-specifically expressed HDAC subtypes, some are known to play important roles in the development and differentiation of normal tissues (Non-Patent Documents 35 and 36).

HDAC6 is an enzyme which is shuttled between the nucleus and the cytoplasm by nucleo-cytoplasmic transport, and which normally locates in the cytoplasm (Non-Patent Document 37). HDAC6 is highly expressed in the testes, and is presumed to relate to the differentiation of normal tissues. Furthermore, HDAC6 is known to be associated with microtubule deacetylation, and to control microtubule stability (Non-Patent Document 38). HDAC6 is also a deacetylation enzyme bonded to a microtubule and affecting cell mobility (Non-Patent Document 39). Accordingly, HDAC6 inhibitors may find utility as metastasis-suppressing agents. TSA inhibits each HDAC subtype to about the same degree. However, HDAC6 cannot be inhibited by trapoxins comprising cyclic tetrapeptide structure and epoxyketone as active groups (Non-Patent Document 40). Based on the information on the three-dimensional structure of the enzyme, trapoxins are presumed to exert poor binding properties to HDAC6 due to the structure of its cyclic tetrapeptide moiety that interacts with the weakly conserved outward surface of the enzyme active center. Accordingly, altering the cyclic tetrapeptide portion may result in inhibitors that are selective for a variety of HDAC.

TSA shows inhibitory activity due to the coordination of its hydroxamic acid group with zinc in the HDAC active pocket (Non-Patent Document 41). Examples of known HDAC inhibitors comprising hydroxamic acid include Oxamflatin (Non-Patent Document 42) and CHAP (Non-Patent Documents 40 and 43). However, TSA is unstable in blood and has a strong hydroxamic acid chelating function. It also chelates with other essential metal ions. Therefore, HDAC inhibitors comprising hydroxamic acid have not actually been used as antitumor agents to date. Meanwhile, thiol groups produced by the reduction of FK228 disulfide bonds have recently been shown to serve as active groups to be coordinated with zinc in the HDAC active pocket, thereby inhibiting HDAC. Thus, FK228 is a prodrug that is activated when reduced by cellular reducing activity (Non-Patent Document 44).

Furthermore, a number of HDAC inhibitors comprising cyclic tetrapeptide structures and epoxyketones as active groups have been isolated Tom natural environments. On the basis of such findings, the cyclic tetrapeptide structure is suggested to be useful in enzyme identification (Yoshida, et al., 1995, supra); however, from various viewpoints such as stability, existing inhibitors have not advanced to the level of being satisfactorily qualified to be pharmaceutical products. Therefore, production of pharmaceutical agents in which these problematic points have been resolved is strongly anticipated.

Prior art documents relating to the invention of the present application are listed below.
[Non-Patent Document 1] Marks, P. A., Richon, V. M., and Rifkind, R. A. (2000) Histone deacetylase inhibitors:

Inducers of differentiation or apoptosis of transformed cells. J. Natl. Cancer Inst. 92, 1210-1216

[Non-Patent Document 2] Yoshida, M., Horinouchi, S., and Beppu, T. (1995) Trichostatin A and trapoxin: novel chemical probes for the role of histone acetylation in chromatin structure and function. Bioessays 17, 423-430

[Non-Patent Document 3] Bernhard, D., Loffler, M., Hartmann, B. L., Yoshida, M., Kofler, R., and Csordas, A. (1999) Interaction between dexamethasone and butyrate in apoptosis induction: non-additive in thymocytes and synergistic in a T cell-derived leukemia cell line. Cell Death Diff. 6, 609-617

[Non-Patent Document 4] Nakajima, H., Kim, Y. B., Terano, H., Yoshida, M., and Horinouchi, S. (1998). FR901228, a potent antitumor antibiotic, is a novel histone deacetylase inhibitor. Exp. Cell Res. 241, 126-133

[Non-Patent Document 5] Saito, A., Yamashita, T., Mariko, Y., Nosaka, Y., Tsuchiya, K., Ando, T., Suzuki, T., Tsuruo, T., and Nakanishi, O. (1999) A synthetic inhibitor of histone deacetylase, MS-27-275, with marked in vivo antitumor activity against human tumors. Proc. Natl. Acad. Sci. USA 96, 4592-4597

[Non-Patent Document 6] Yoshida, M., Kijima, M., Akita, M., and Beppu, T. (1990) Potent and specific inhibition of mammalian histone deacetylase both in vivo and in vitro by trichostatin A. J. Biol. Chem. 265, 17174-17179

[Non-Patent Document 7] Yoshida, M., Nomura, S., and Beppu, T. (1987) Effects of trichostatins on differentiation of murine erythroleukemia cells. Cancer Res. 47: 3688-3691

[Non-Patent Document 8] Hoshikawa, Y., Kijima, M., Yoshida, M., and Beppu, T. (1991) Expression of differentiation-related markers in teratocarcinoma cells via histone hyperacetylation by trichostatin A. Agric. Biol. Chem. 55: 1491-1495

[Non-Patent Document 9] Minucci, S., Horn, V., Bhattacharyya, N., Russanova, V., Ogryzko, V. V., Gabriele, L., Howard, B. H., and Ozato, K. (1997) A histone deacetylase inhibitor potentiates retinoid receptor action in embryonal carcinoma cells. Proc. Natl. Acad. Sci. USA 94: 11295-11300

[Non-Patent Document 10] Inokoshi, J., Katagin, M., Arima, S., Tanaka, H., Hayashi, M., Kim, Y. B., Furumai, R., Yoshida, M., Horinouchi, S., and Omura, S. (1999) Neuronal differentiation of Neuro 2a cells by inhibitors of cell progression, trichostatin A and butyrolactone I. Biochem. Biophys. Res. Commun. 256, 372-376

[Non-Patent Document 11] Wang, J., Saunthararajah, Y., Redner, R. L., and Liu, J. M. (1999) Inhibitors of histone deacetylase relieve ETO-mediated repression and induce differentiation of AML1-ETO leukemia cells. Cancer Res. 59: 2766-2769

[Non-Patent Document 12] Munster, P. N., Troso-Sandoval, T., Rosen, N., Rifkind, R., Marks, P. A., and Richon, V. M. (2001) The histone deacetylase inhibitor suberoylanilide hydroxamic acid induces differentiation of human breast cancer cells. Cancer Res. 61: 8492-8497

[Non-Patent Document 13] Ferrara, F. F., Fazi, F., Bianchini, A., Padula, F., Gelmetti, V., Minucci, S., Mancini, M., Pelicci, P. G., Lo Coco, F., and Nervi, C. (2001) Histone deacetylase-targeted treatment restores retinoic acid signaling and differentiation in acute myeloid leukemia Cancer Res. 61: 2-7

[Non-Patent Document 14] Gottlicher, M., Minucci, S., Zhu, P., Kramer, O. H., Schimpf, A., Giavara, S., Sleeman, J. P., Lo Coco, F., Nervi, C., Pelicci, P. G., and Heinzel, T. (2001) Valproic acid defines a novel class of HDAC inhibitors inducing differentiation of transformed cells. EMBO J. 20: 6969-6978

[Non-Patent Document 15] Coffey, D. C., Kutko, M. C., Glick, R. D., Butler, L. M., Heller, G., Rifkind, R, A., Marks, P. A., Richon, V. M., and La Quaglia, M. P. (2001) The histone deacetylase inhibitor, CBHA, inhibits growth of human neuroblastoma xenografts in vivo, alone and synergistically with all-trans retinoic acid. Cancer Res. 61: 3591-3594

[Non-Patent Document 16] Petti, M. C., Fazi, F., Gentile, M., Diverio, D., De Fabritiis, P., De Propris, M. S., Fiorini, R., Spiriti, M. A., Padula, F., Pelicci, P. G., Nervi, C., and Lo Coco, F. (2002) Complete remission through blast cell differentiation in PLZF/RARalpha-positive acute promyelocytic leukemia: in vitro and in vivo studies. Blood 100: 1065-1067

[Non-Patent Document 17] Nan, X., Ng, H. H., Johnson, C. A., Laherty, C. D., Turner, B. M., Eisenman, R. N., and Bird, A. (1998) Transcriptional repression by the methyl-CpG-binding protein MeCP2 involves a histone deacetylase complex. Nature 393: 386-389

[Non-Patent Document 18] Cameron, E. E., Bachman, K. E., Myohanen, S., Herman, J. G., and Baylin, S. B. (1999) Synergy of demethylation and histone deacetylase inhibition in the re-expression of genes silenced in cancer. Nature Genet. 21: 103-107

[Non-Patent Document 19] Li, Q. L., Ito, K., Sakakura, C., Fukamachi, H., Inoue, K., Chi, X. Z., Lee, K. Y., Nomura, S., Lee, C. W., Han, S. B., Kim, H. M., Kim, W. J., Yamamoto, H., Yamashita, N., Yano, T., Ikeda, T., Itohara, S., Inazawa, J., Abe, T., Hagiwara, A., Yamagishi, H., Ooe, A., Kaneda, A., Sugimura, T., Ushijima, T., Bae, S. C., and Ito, Y. (2002) Causal relationship between the loss of RUNX3 expression and gastric cancer. Cell 109: 113-124

[Non-Patent Document 20] Boivin, A. J., Momparler, L. F., Hurtubise, A., and Momparler, R. L. (2002) Atineoplastic action of 5-aza-2'-deoxycytidine and phenylbutyrate on human lung carcinoma cells. Anticancer Drugs 13: 969-874

[Non-Patent Document 21] Primeau, M., Gagnon, J., and Momparler, R. L. (2003) Synergistic antineoplastic action of DNA methylation inhibitor 5-AZA-2'-deoxycytidine and histone deacetylase inhibitor depsipeptide on human breast carcinoma cells. Int J Cancer 103; 177-184

[Non-Patent Document 22] Darkin-Rattray S J, Gurnett A M, Myers R W, Duiski P M, Crumley T M, Allocco J J, Cannova C, Meinke P T, Colletti S L, Bednarek M A, Singh S B, Goetz M A, Dombrowski A W, Polishook J D, Schmatz D M. (1996) a novel antiprotozoal agent that inhibits parasite histone deacetylase. Proc. Natl. Acad. Sci. USA 93, 13143-13147

[Non-Patent Document 23] Steffan J S, Bodai L, Pallos J, Poelman M, McCampbell A, Apostol B L, Kazantsev A, Schmidt E, Zhu Y Z, Cireenwald M, Kurokawa R, Housman D E, Jackson G R, Marsh J L, Thompson L M. (2001) Histone deacetylase inhibitors arrest polyglutamine-dependent neurodegeneration in *Drosophila*. Nature. 413 739-43

[Non-Patent Document 24] McCampbell A, Taye A A, Whitty L, Penney E, Steffan J S, Fischbeck K H. (2001) Histone deacetylase inhibitors reduce polyglutamine toxicity. Proc Natl Acad Sci USA.: 98 15179-15184

[Non Patent Document 25] Dion L D, Goldsmith K T, Tang D C, Engler J A, Yoshida M, Garver R I Jr. (1997) Amplification of recombinant adenoviral transgene products occurs by inhibition of histone deacetylase. Virology 231, 201-209

[Non-Patent Document 26] Chen W Y, Bailey E C, McCune S L, Dong J Y, Townes T M. (1997) Reactivation of silenced, virally transduced genes by inhibitors of histone deacetylase. Proc. Natl. Acad. Sci. USA 94, 5798-5803

[Non-Patent Docurxaent 27] Kim, M. S., Kwon, H. J., Lee, Y. M., Baek, J. H., Jang, J. E., Lee, S. W., Moon, E. J., Kim, H. S., Lee, S. K., Chung; H. Y., Kim, C. W., and Kim, K. W. (2001) Histone deacetylases induce angiogenesis by negative regulation of tumor suppressor genes. Nature Med. 7, 437-443

[Non-Patent Document 28] Kwon, H. J., Kim, M. S., Kim, M. J., Nakajima, H., and Kim, K. W. (2002) Histone deacetylase inhibitor PK228 inhibits tumor angiogenesis. Int. J. Cancer 97, 290-296

[Non-Patent Document 29] Ito, A., Lai, C. H., Zhao, X., Saito, S., Hamilton, M. H., Appella, E., and Yao, T. P. (2001) p300/CBP-mediated p53 acetylation is commonly induced by p53-activating agents and inhibited by MDM2. EMBO J. 20, 1331-1340

[Non-Patent Document 30] Juan, L. J., Shia, W. J., Chen, M. H., Yang, W. M., Seto, E., Lin, Y. S., and Wu, C. W. (2000) Histone Deacetylases Specifically Down-regulate p53-dependent Gene Activation. J. Biol. Chem. 275, 20436-20443

[Non-Patent Document 31] Dhordain P., Albaghi, O., Lin, R. J., Ansieau, S., Quief, S., Leutz, A., Kerckaert, J. P., Evans, R. M., and Leprince, D. (1997) Corepressor SMRT binds the BTB/POZ repressing domain of the LAZ3/BCL6 oncoprotein. Proc. Natl. Acad. Sci. USA 94, 10762-10767

[Non-Patent Document 32] Grignani, F., De, M. S., Nervi, C., Tomassoni, L., Gelmetti, V., Cioce, M., Fanelli, M., Ruthardt, M., Ferrara, F. F., Zamir, I., Seiser, C., Grignani, F., Lazar, M. A., Minucci, S., and Pelicci, P. G. (1998) Fusion proteins of the retinoic acid receptor-alpha recruit histone deacetylase in promyelocytic leukaemia. Nature 391, 815-818

[Non-Patent Document 33] He, L. Z., Guidez, F., Tribioli, C., Peruzzi, D., Ruthardt, M., Zelent, A., and Pandolfi, P. P. (1998) Distinct interactions of PML-RARalpha and PLZF-RARalpha with co-repressors determine differential responses to RA in APL. Nature Genet. 18, 126-135

[Non-Patent Document 34] Lin, R. J., Nagy, L., Inoue, S., Shao, W., Miller, W. J., and Evans, R. M. (1998) Role of the histone deacetylase complex in acute promyelocytic leukaemia. Nature 391, 811-814

[Non-Patent Document 35] McKinsey, T. A., Zhang, C. L., Lu, J., and Olson, E. N. (2000) Signal-dependent nuclear export of a histone deacetylase regulates muscle differentiation. Nature 408, 106-111

[Non-Patent Document 36] Verdel, A., and Khochbin, S. (1999) Identification of a new family of higher eukaryotic histone deacetylases. Coordinate expression of differentiation-dependent chromatin modifiers. J. Biol. Chem. 274, 2440-2445

[Non-Patent Document 37] Verdel, A., Curtet, S., Brocard, M.-P., Rousseaux, S., Lemercier, C., Yoshida, M., and Khochbin, S. (2000) Active maintenance of mHDA2/mHDAC6 histone-deacetylase in the cytoplasm. Curr. Biol. 10, 747-749

[Non-Patent Document 38] Matsuyama, A., Shimazu, T., Sumida, Y., Saito, A., Yoshimatsu, Y., Seigneurin-Berny, D., Osada, H., Komatsu, Y., Nishino, N., Khochbin, S., Horinouchi, S., and Yoshida, M. (2002) In vivo destabilization of dynamic microtubules by HDAC6-mediated deacetylation. EMBO J. 21, 6820-6831

[Non-Patent Document 39] Hubbert, C., Guardiola, A., Shao, R., Kawaguchi, Y., Ito, A., Nixon, A., Yoshida, M., Wang, X.-F., and Yao, T.-P. (2002) HDAC6 is a microtubule-associated deacetylase. Nature 417, 455-458

[Non-Patent Document 40] Furumai, R., Komatsu, Y., Nishino, N., Khochbin, S., Yoshida, M., and Horinouchi, S. (2001) Potent histone deacetylase inhibitors built from trichostatin A and cyclic tetrapeptide antibiotics including trapoxin. Proc. Natl. Acad. Sci. USA 98: 87-92

[Non-Patent Document 41] Finnin, M. S., Donigian, J. R., Cohen, A., Richon, V. M., Rifkind, R. A., Marks, P. A., Breslow, R., and Pavletich, N. P. (1999) Structures of a histone deacetylase homologue bound to the TSA and SAHA inhibitors. Nature 401: 188-193

[Non-Patent Document 42] Kim, Y. B., Lee, K.-H., Sugita, K., Yoshida, M., and Horinouchi, S. (1999) Oxamflatin is a novel antitumor compound that inhibits mammalian histone deacetylase. Oncogene 18: 2461-2470

[Non-Patent Document 43] Komatsu, Y., Tomizaki, K.-y., Tsukamoto, M., Kato, T., Nishino, N., Sato, S., Yamori, T., Tsuruo, T., Furumai, R., Yoshida, M., Horinouchi, S., and Hayashi, H. (2001) Cyclic Hydroxamic-acid-containing Peptide 31, a potent synthetic histone deacetylase inhibitor with antitumor activity. Cancer Res. 61: 4459-4466

[Non-Patent Document 44] Furumai, R., Matsuyama, A., Kobashi, N., Lee, K.-H., Nishiyama, M., Nakajima, H., Tanaka, A., Komatsu, Y., Nishino, N., Yoshida, M., and Horinouchi, S. (2002) FK228 (depsipeptide) as a natural prodrug that inhibits class I histone deacetylases. Cancer Res. 62, 4916-4921

Disclosure of the Invention

An objective of the present inventors is to provide novel HDAC inhibitors comprising a cyclic tetrapeptide structure and methods for producing them.

In view of the above circumstances, the present inventors synthesized compounds with cyclic tetrapeptide structures and various functional groups, such compounds being able to coordinate with the zinc positioned at the active center of histone deacetylase, and analyzed their HDC inhibitory activity. As a result, strong HDAC inhibitory activity was demonstrated, both in vitro and in vivo, for those compounds including a carbonyl group, a fluoro group, or a retrohydroxamate group. When the activities of these compounds were analyzed at the cellular level, a strong activity similar to that of Trichostatin A (TSA), a known HDAC inhibitor, was observed. These compounds not only inhibited the deacetylation of histone but also inhibited the deacetylation of tubulin. Thus, these compounds showed strong activity in cells, indicating their utility as HDAC inhibitors.

Specifically, the present invention relates to HDAC inhibitors and methods for producing them, and provides [1] to [11] described below.

[1] A compound represented by formula (1)

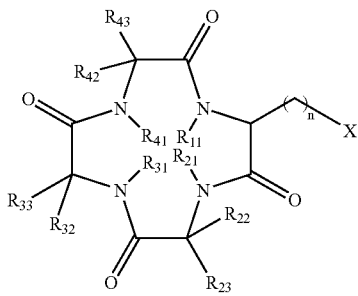

wherein $R_{11}, R_{21}, R_{31},$ and $R_{41}$, independently represent a hydrogen or methyl group;

$R_{22}, R_{23}, R_{32}, R_{33}, R_{42},$ and $R_{43}$ independently represent any one of hydrogen, a linear alkyl group comprising 1 to 6 carbons, a linear alkyl group comprising 1 to 6 carbons to which a non-aromatic cyclic alkyl group or a substituted or unsubstituted aromatic ring is attached, a non-aromatic cyclic alkyl group, or a non-aromatic cyclic alkyl group to which a non-aromatic cyclic alkyl group or a substituted or unsubstituted aromatic ring is attached;

$R_{21}$ and $R_{22}$, $R_{22}$ and $R_{23}$, $R_{31}$ and $R_{32}$, $R_{32}$ and $R_{33}$, $R_{41}$ and $R_{42}$, and $R_{42}$ and $R_{43}$ may independently represent a non-cyclic structure without bonding to each other, or may independently represent a cyclic structure by bonding to each other through a linear alkylene group having a chain length of 1 to 5 carbons, a linear alkylene chain having a chain length of 1 to 5 carbons and carrying a branched chain of 1 to 6 carbon atoms, or a linear alkylene chain having a chain length of 1 to 5 carbons and carrying a cyclic structure of 1 to 6 carbon atoms;

n can be selected from a range of numbers that enable the compound to have HDAC inhibitory activity; and X represents a structural component having a structure that can coordinate with the zinc positioned at the active center of histone deacetylase.

[2] The compound of [1], wherein X is any one of the substituents represented by the following structural formulas:

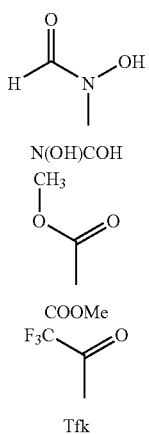

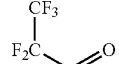

Pfek

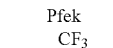

Mtfk

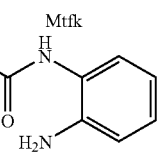

OPD

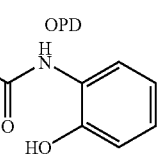

OAPOH

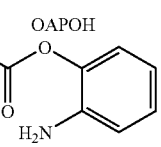

OAPNH

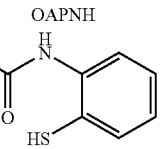

OATP

[3] A histone deacetylase inhibitor comprising the compound of [1] as an active ingredient.

[4] A tubulin deacetylase inhibitor comprising the compound of [1] as an active ingredient.

[5] An apoptosis inducer comprising the compound of [1] as an active ingredient.

[6] A differentiation inducer comprising the compound of [1] as an active ingredient.

[7] An angiogenesis inhibitor comprising the compound of [1] as an active ingredient.

[8] A cancer metastasis inhibitor comprising the compound of [1] as an active ingredient.

[9] A pharmaceutical agent for treatment or prevention of a disease caused by histone deacetylase 1, 4, or 6, wherein the agent comprises the compound of [1] as an active ingredient.

[10] The pharmaceutical agent for treatment or prevention of [9], wherein the disease caused by histone deacetylase 1, 4, or 6 is cancer, autoimmune disease, neurodegenerative disease, skin disease, or infection.

[11] A method for producing the compound of [1], wherein the method comprises reacting a compound represented by formula (2)

(2)

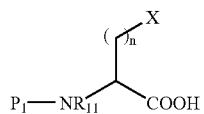

(wherein X are as defined in claims 1 and 2, and $P_1$ represents an amino protecting group) with a compound represented by formula (3)

(3)

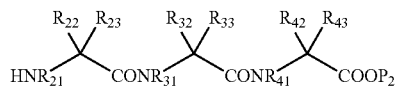

(wherein $R_{11}$, $R_{21}$, $R_{22}$, $R_{23}$, $R_{31}$, $R_{32}$, $R_{33}$, $R_{41}$, $R_{42}$, and $R_{43}$ are as defined in formula (1), and $P_2$ represents a carboxyl protecting group) in the presence of a peptide coupling agent to yield a compound represented by formula (4)

(4)

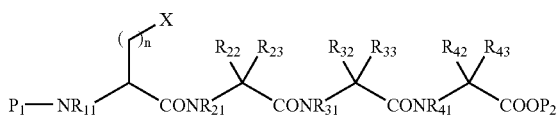

(wherein n, $R_{11}$, $R_{21}$, $R_{22}$, $R_{23}$, $R_{31}$, $R_{32}$, $R_{33}$, $R_{41}$, $R_{42}$, $R_{43}$, $P_1$, $P_2$, and X are as defined above), then subjecting the compound represented by formula (4) to catalytic hydrogenation, acid treatment, or hydrolysis to remove $P_1$ and $P_2$, and subsequently, carrying out a cyclization reaction in the presence of a peptide coupling agent;

reacting a compound represented by formula (5)

(5)

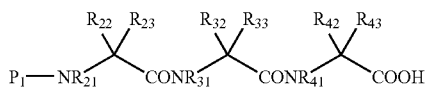

(wherein $R_{21}$, $R_{22}$, $R_{23}$, $R_{31}$, $R_{32}$, $R_{33}$, $R_{41}$, $R_{42}$, $R_{43}$, and $P_1$ are as defined above) with a compound represented by formula (6)

(6)

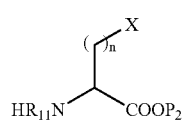

(wherein n, $R_{11}$, $P_2$, and X are as defined above) in the presence of a peptide coupling agent to yield a compound represented by formula (7)

(7)

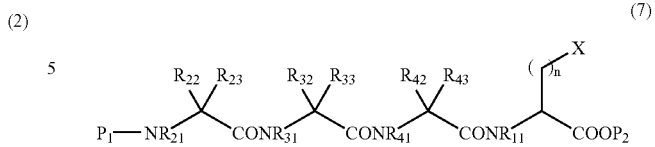

(wherein n, $R_{11}$, $R_{21}$, $R_{22}$, $R_{23}$, $R_{31}$, $R_{32}$, $R_{33}$, $R_{41}$, $R_{42}$, $R_{43}$, $P_1$, $P_2$, and X are as defined above), then subjecting the compound represented by formula (7) to catalytic hydrogenation, acid treatment, fluoride anion treatment, or hydrolysis to remove $P_1$ and $P_2$, and subsequently, carrying out a cyclization reaction in the presence of a peptide coupling agent; or reacting a compound in which X of the cyclic tetrapeptide of formula (1) is a carboxyl group or a sulfhydryl group individually with trifluoroacetic anhydride, pentafluoropropanoic anhydride, or 1,1,1-trifluoro-3-bromoacetone to change substituent X into a different type of substituent.

The embodiments of the present invention are described in detail below with reference to drawings.

The compounds of the present invention can be represented by formula (1). These compounds can be used as HDAC inhibitors.

In formula (1), $R_{11}$, $R_{21}$, $R_{31}$, and $R_{41}$ independently represent a hydrogen or methyl group. $R_{22}$, $R_{23}$, $R_{32}$, $R_{33}$, $R_{42}$, and $R_{43}$ independently represent any one of the following: hydrogen, a linear alkyl group comprising 1 to 6 carbons, a linear alkyl group comprising 1 to 6 carbons to which a non-aromatic cyclic alkyl group or a substituted or unsubstituted aromatic ring is attached, a non-aromatic cyclic alkyl group, or a non-aromatic cyclic alkyl group to which a non-aromatic cyclic alkyl group or a substituted or unsubstituted aromatic ring is attached.

$R_{21}$, and $R_{22}$, $R_{22}$ and $R_{23}$, $R_{31}$ and $R_{32}$, $R_{32}$ and $R_{33}$, $R_{41}$ and $R_2$, and $R_{42}$ and $R_{43}$ may independently represent a non-cyclic structure without linking to each other, or, alternatively, may form a cyclic structure by bonding to each other through a linear alkylene group having a chain length of 1 to 5 carbons, a linear alkylene group having a chain length of 1 to 5 carbons and carrying a branched chain of 1 to 6 carbon atoms, or a linear alkylene group having a chain length of 1 to 5 carbons and carrying a cyclic structure of 1 to 6 carbon atoms. This cyclic tetrapeptide structure may function as a cap for the HDAC pocket; therefore, so long as the structure can function as the cap, any of the above-mentioned linear alkyl groups comprising 1 to 6 carbon atoms, aromatic cyclic alkyl groups, or aromatic groups that may become their substituents can be selected.

In formula (1), X denotes a discretionary structural component having a structure that enables coordination with the zinc positioned at the active center of histone deacetylase. If X comprises a highly reactive functional group substituent, this compound will be unstable in vivo. Therefore, when X is a highly reactive functional group, the compound is preferably used in combination with means that would allow stable transport of the compound to a desired site, such as a drug delivery system. To increase the stability of functional groups having HDAC inhibitory activity, the use of a substituent that is metabolized in vivo and is not harmful to the body is preferred. A substituent carrying a ketone-type zinc ligand on its side chain is preferred for such a substituent; the substituent itself may have some therapeutic effect, or, alternatively, it may simply function as a protecting group.

Examples of preferred structures for substituent X are shown below.

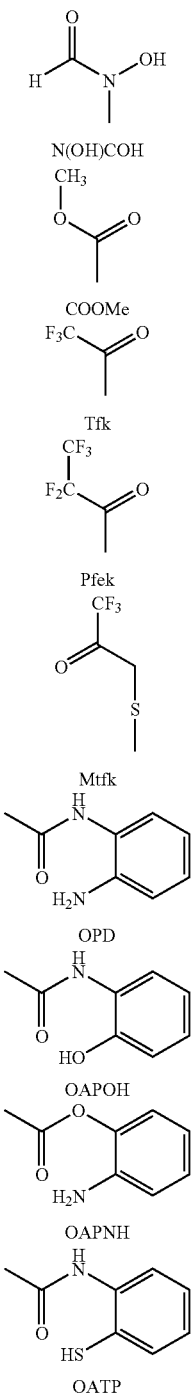

N(OH)COH

COOMe

Tfk

Pfek

Mtfk

OPD

OAPOH

OAPNH

OATP

In formula (1) of the present invention, n can be selected from a range of numbers that enable the compound to have HDAC inhibitory activity; for example, n is preferably 4 to 6, and most preferably 5. The carbon chain extending from this cyclic tetrapeptide structure and comprising n carbons may enter the active pocket of HDAC, and thereby have the function of inhibiting HDAC by contacting the various functional groups positioned at the tip of this carbon chain with the zinc molecule in the pocket of HDAC.

Methods for producing the compounds of the present invention are described below. Embodiments of the present invention can be produced as follows, using compounds represented by formula (2) or (6) as the starting compound. Since n, $R_{11}$, $R_{21}$, $R_{22}$, $R_{23}$, $R_{31}$, $R_{32}$, $R_{33}$, $R_{41}$, $R_{42}$, $R_{43}$, $P_1$, $P_2$, X, and the like have the same mean as defined above, their definitions are not reiterated here.

The first embodiment of the method for producing the compounds of the present invention is a production method that uses a compound represented by formula (2), shown below, as the starting compound. More specifically, a compound represented by formula (2)

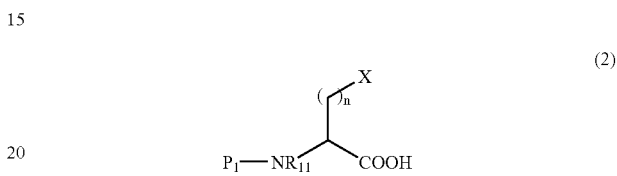

(2)

(in X, protecting groups can be attached to a certain part of its substituent which would otherwise undergo some type of modification and substitution due to chemical reactions that follow) and a compound represented by formula (3)

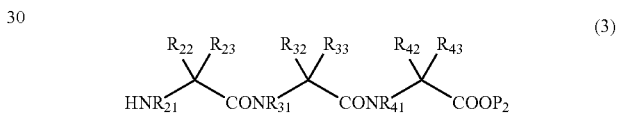

(3)

are reacted with each other in the presence of a peptide coupling agent to yield a compound represented by formula (4).

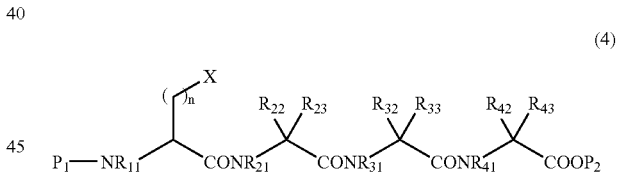

(4)

In these formulas, X represents a substituent shown in FIG. 2, and $P_2$ represents an amino protecting group.

Next, the compound represented by formula (4) is subjected to catalytic hydrogenation, acid treatment, fluoride anion treatment, or hydrolysis to remove $P_1$ and $P_2$. Finally, a cyclization reaction is carried out in the presence of a peptide coupling agent to yield the compound represented by formula (1). When a protecting group is attached in advance to a particular site on X of formula (2), a step to remove the protecting group by catalytic hydrogenation, acid treatment, fluoride anion treatment, or hydrolysis can be included as the last step.

The second embodiment of the method for producing the compounds of the present invention is a production method that uses a compound represented by formula (6) as the starting compound. Specifically, a compound represented by formula (5)

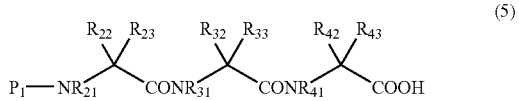

is reacted with a compound represented by formula (6)

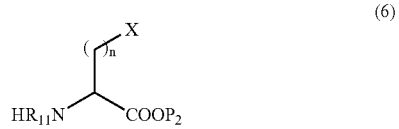

(in X, when a certain part of its substituent undergoes some type of modification and substitution due to chemical reactions that follow, protecting groups can be attached to the part that undergoes the modification and substitution) in the presence of a peptide coupling agent to yield a compound represented by formula (7).

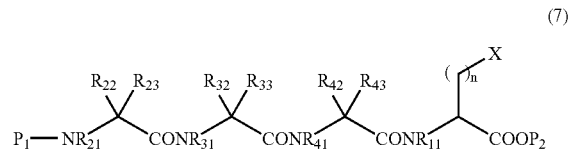

Then, the compound represented by formula (7) is subjected to catalytic hydrogenation, acid treatment, fluoride anion treatment, or hydrolysis to remove $P_1$ and $P_2$. Finally, a cyclization reaction is carried out in the presence of a peptide coupling agent to give the compound represented by formula (1). When a protecting group is attached in advance to a particular site on X of formula (2), a step to remove the protecting group by catalytic hydrogenation, acid treatment, fluoride anion treatment, or hydrolysis can be included as the last step. Compounds in which X of the cyclic tetrapeptide of formula (1) is a carboxyl group or a sulfhydryl group are reacted individually with trifluoroacetic anhydride, pentafluoropropanoic anhydride, or 1,1,1-trifluoro-3-bromoacetone to produce compounds represented by formula (1) carrying different types of substituent X.

HDAC-inhibiting compounds are known to induce differentiation of cancer cells, leukemia cells, and neural cells, to induce apoptosis, and to suppress cancer cell metastasis (Yoshida, M., Nomura, S., and Beppu, T. (1987) Effects of trichostatins on differentiation of murine erythroleukemia cells. Cancer Res. 47: 3688-3691; Hoshikawa, Y., Kijima, M., Yoshida, M., and Beppu, T. (1991) Expression of differentiation-related markers in teratocarcinoma cells via histone hyperacetylation by trichostatin A. Agric. Biol. Chem. 55: 1491-1495; Minucci, S., Horn, V., Bhattacharyya, N., Russanova, V., Ogryzko, V. V., Gabriele, L., Howard, B. H., and Ozato, K. (1997) A histone deacetylase inhibitor potentiates retinoid receptor action in embryonal carcinoma cells. Proc. Natl. Acad. Sci. USA 94: 11295-11300; Inokoshi, J., Katagiri, M., Axima, S., Tanaka, H., Hayashi, M., Kim, Y. B., Furumai, R., Yoshida, M., Horinouchi, S., and Omura, S. (1999). Neuronal differentiation of Neuro 2a cells by inhibitors of cell progression, trichostatin A and butyrolactone I. Biochem. Biophys. Res. Commun. 256, 372-376; Wang, J., Saunthararajah, Y., Redner, R. L., and Liu, J. M. (1999) Inhibitors of histone deacetylase relieve ETO-mediated repression and induce differentiation of AML1-ETO leukemia cells. Cancer Res. 59: 2766-2769; Munster, P. N., Troso-Sandoval, T., Rosen, N., Rifkind, R., Marks, P. A., and Richon, V. M. (2001) The histone deacetylase inhibitor suberoylanilide hydroxamic acid induces differentiation of human breast cancer cells. Cancer Res. 61: 8492-8497; Ferrara, F. F., Fazi, F., Bianchini, A., Padula, F., Gelmetti, V., Minucci, S., Mancini, M., Pelicci, P. G., Lo Coco, F., and Nervi, C. (2001) Histone deacetylase-targeted treatment restores retinoic acid signaling and differentiation in acute myeloid leukemia. Cancer Res. 61: 2-7; Gottlicher, M., Minucci, S., Zhu, P., Kramer, O. H., Schimpf, A., Giavara, S., Sleeman, J. P., Lo Coco, F., Nervi, C., Pelicci, P. G., and Heinzel, T. (2001) Valproic acid defines a novel class of HDAC inhibitors inducing differentiation of transformed cells. EMBO J. 20: 6969-6978). Accordingly, the compounds of the present invention can be utilized as apoptosis-inducing agents, differentiation-inducing agents, and cancer-metastasis-suppressing agents.

Also, the HDAC inhibitors are expected to inhibit angiogenesis (Kim, M. S., Kwon, H. J., Lee, Y. M., Baek, J. H., Jang, J. E., Lee, S. W., Moon, B. J., Kim, H. S., Lee, S. K., Chung, H. Y., Kim, C. W., and Kim, K. W. (2001). Histone deacetylases induce angiogenesis by negative regulation of tumor suppressor genes. Nature Med. 7, 437-443; Kwon, H. J., Kim, M. S., Kim, M. J., Nakajima, H., and Kim, K. W. (2002). Histone deacetylase inhibitor FK228 inhibits tumor angiogenesis. Int. J. Cancer. 97, 290-296). Thus, the compounds of the present invention can also be utilized as angiogenesis inhibitors.

Among HDACs, the compounds of the present invention exhibit a strong inhibitory activity to HDAC1, 4, and 6. Therefore, the compounds of the present invention are useful as pharmaceutical agents for treating or preventing diseases caused by HDAC1, 4, or 6. Examples of such diseases, in addition to cancer, include autoimmune diseases, neurodegenerative diseases, skin diseases, and infectious diseases associated with HDAC1, 4, or 6. Furthermore, the compounds of the present invention may be applied not only to pharmaceutical agents for treating or preventing the above-mentioned diseases, but also to gene therapy adjuvants or accelerating agents that improve the efficiency of vector introduction, promote the expression of introduced genes, and the like.

The compounds of the present invention may also be used in combination with retinoic acids and DNA methylation inhibitors. The invention also provides such concomitant agents.

When formulating the compounds of the present invention, diluents or vehicles, such as fillers, extenders, binders, moisturizing agents, disintegrators, surfactants, and lubricants, may be used as necessary. Furthermore, coloring agents, preservatives, aromatics, flavors, sweeteners, and other pharmaceuticals may be added to the pharmaceutical formulations. The form of each type of pharmaceutical formulation may be selected depending upon its therapeutic or preventative purpose. For example, the pharmaceutical formulation may take the form of a tablet, pill, powder, solution, suspension, emulsion, granule, capsule, injection, or suppository.

Examples of additives to be added to tablets and capsules include binders, such as gelatin, corn starch, tragacanth gum, and acacia; vehicles, such as crystalline cellulose; swelling agents, such as corn starch, gelatin, and alginic acid; lubricants, such as magnesium stearate; sweeteners, such as sucrose, lactose, and saccharine; and aromatics, such as peppermint, Gaultheria adenothrix oil, and cherry. In the case where the unit dosage form is a capsule, a liquid carrier, such as oil or fat, can be added in addition to the above-mentioned materials.

As an aqueous solution for injection, an isotonic solution of, for example, D-sorbitol, D-mannose, D-mannitol, or sodium chloride comprising saline, glucose, and other adjuvants may also be used as necessary in combination with a proper dissolution-assisting agent, such as an alcohol, specifically, ethanol; a polyalcohol, such as propylene glycol and polyethylene glycol; or a nonionic surfactant, such as polysorbate 80™ and HCO-50.

Examples of oleaginous solutions are sesame oil and soybean oil, which can be used, as necessary, in combination with a dissolution-assisting, agent, such as benzyl benzoate and benzyl alcohol. Furthermore, mixing with a buffer, such as phosphate buffer solution or sodium acetate buffer solution; a soothing agent, such as procaine hydrochloride; a stabilizer, such as benzyl alcohol and phenol; or an antioxidant is also acceptable. The formulated injection is generally filled into suitable ampules.

Formulations may be administered to patients orally or parenterally. Examples of a parenteral dosage form include injection as well as transnasal, transpulmonal, and transdermal administration. Systemic or local administration can be carried out using an injection dosage form, such as an intravenous injection, intramuscular injection, intraperitoneal injection, or subcutaneous injection. Furthermore, intranasal, transbronchial, intramuscular, subcutaneous, or oral administration may also be carried out by methods known to those skilled in the art.

For parenteral administration, the unit dosage of the compounds of the present invention depends on the subjects to be administrated, the target organs, symptoms, and the manner of administration. For example, it is preferable that injections be administered intravenously to adults (60 kg body weight) at a dosage of about 0.01 to 30 mg per day, preferably about 0.1 to 20 mg per day, and more preferably about 0.1 to 10 mg per day. When administering to other kinds of animals, dosages can be converted per 60 kg body weight, or per unit of body surface area.

For oral administration, the unit dosage of the compounds of the present invention depends on the subjects to be administrated, the target organs, symptoms, and manner of administration, and is generally, for example, about 100 μg to 20 mg per day for an adult (60 kg body weight).

All prior art documents cited herein are incorporated by reference into this specification.

BEST MODE FOR CARRYING OUT THE INVENTION

Figure 1:
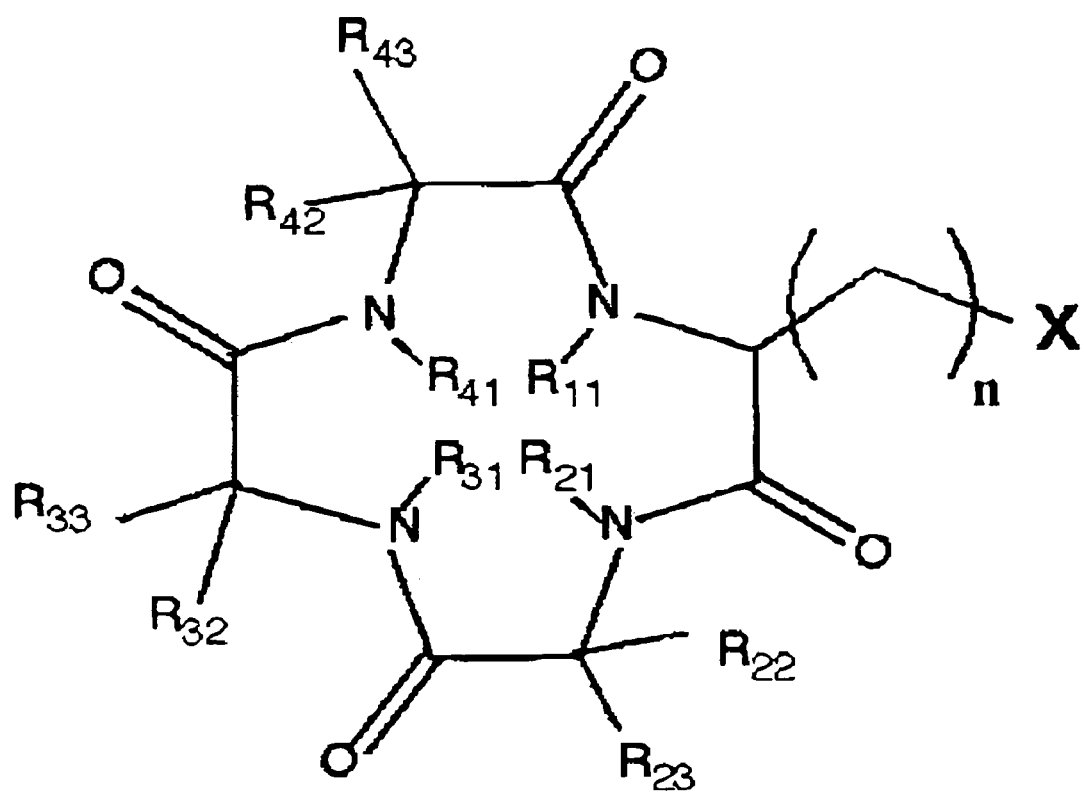
FIG. 1 depicts the compound of formula (1).

The present invention is explained in detail below with reference to Examples; however, it is not to be construed as being limited thereto.

The synthesis steps for each of the compounds of the present invention are described in detail below. The abbreviations used herein are "Ab6" for 2-amino-6-bromohexanoic acid, "Am6(Ac)" for 2-amino-6-acetylthiohexanoic acid, "Am6(Tfacet)" for 2-amino-6-(3',3',3'-trifluoracetonylthio)-hexanoic acid, "A2oc" for 2,8-diaminooctanoic acid, "Aph" for 2-amino-7-dimethylphosphonylheptanoic acid, "Asu" for α-aminosuberic acid, "For" for formyl group, "Hly" for homolysine, "Tfm" for 2-amino-8-oxo-9,9,9-trifluorononanoic acid, "Tyr(Me)" for O-methyltyrosine, "Pfe" for 2-amino-8-oxo-9,9,10,10,10-pentafluorodecanoic acid, and "Pip" for pipecolic acid. Additional abbreviations include "OPD" for o-phenylenediamine, "OAPOH" for the amide of o-aminophenol, "OAPNH" for the ester of o-aminophenol, and "OATP" for o-aminothiophenol.

EXAMPLE 1

Synthesis of cyclo(-L-Asu(OMe)-D-Tyr(Me)-L-Ile-D-Pro-)

Cyclo(-L-Asu(OBzl)-D-Tyr(Me)-L-Ile-D-Pro-) (0.150 mmol, 100 mg) synthesized by an existing method was dissolved in MeOH (1 mL). 4 N HCl/dioxane (50 μL) was added to the solution, and this was left to stand at room temperature for 8 hours. The reaction solution was concentrated and purified by silica gel chromatography to yield the desired product as a foam (column: Merck Kieselgel 60 Φ 1.5×15 cm, eluent: CHCl$_3$/MeOH, 99/1). Yield: 65 mg (0.113 mmol, 76%).

EXAMPLE 2

Synthesis of cyclo(-L-Lys(For, OH)-D-Tyr(Me)-L-Ile-L-Pip-) and cyclo(-L-Lys(For, OH)-D-Tyr(Me)-L-Ile-D-Pip-)

(1) Synthesis of Ac-DL-Ab6-OtBu

Ac-DL-Ab6-OH (1.26 g, 50 mmol) was dissolved in DCM (100 mL), and concentrated sulfuric acid (1 mL) was added. While cooling on ice, isobutylene gas (50 mL) was blown into the solution, and this was left to stand at room temperature for 11 days. After adding 4% aqueous sodium bicarbonate solution (80 mL), isobutylene gas was vaporized by leaving the mixture to stand. The DCM solution was washed 3 times each with 10% aqueous citric acid solution, 4% aqueous sodium bicarbonate solution, and saturated brine, and dried over magnesium sulfate, and then DCM was removed by evaporation. Purification of the residue by silica gel chromatography yielded the desired product as a syrup (column: Merck Kieselgel 60 Φ 5.0×10 cm, eluent: CHCl$_3$/MeOH, 49/1). TLC: Rf, 0.8 (CHCl$_3$/MeOH, 49/1). Yield: 9.25 g (30.1 mmol, 60%).

(2) Synthesis of Ac-DL-Lys(OBzl)-OtBu

Ac-DL-Ab6-OtBu (9.25 g, 30 mmol) was dissolved in methanol (120 mL), and O-benzylhydroxylamine hydrochloride salt (9.58 g, 60 mml) and DIEA (20.9 mL, 120 mmol) were added. The mixture was then heated under reflux at 80° C. for 4 days. The reaction solution was concentrated, and then extracted with ethyl acetate. The extract was washed once each with 4% aqueous sodium bicarbonate solution and distilled water, and then dried over sodium carbonate, and ethyl acetate was removed by evaporation. Purification of the residue by silica gel chromatography yielded the desired product as a syrup (column: Merck Kieselgel 60 Φ 5.0×22 cm, eluent: CHCl$_3$/MeOH, 49/1). TLC: Rf, 0.3 (CHCl$_3$/MeOH, 49/1) Yield: 5.13 g (14.6 mmol, 49%).

(3) Synthesis of Ac-DL-Lys(For, OBzl)-OtBu

Formic acid (58 mL) and acetic anhydride (5.4 mL, 50 mmol) were added to Ac-DL-Lys(OBzl)-OtBu (4.01 g, 11.5 mmol) on ice, and the mixture was stirred for 1 hour. The reaction solution was concentrated, and extracted with ethyl acetate. The extract was washed 3 times with water, and then dried over magnesium sulfate, and ethyl acetate was removed by evaporation. Purification of the residue by silica gel chromatography yielded the desired product as a syrup (column: Merck Kieselgel 60 Φ 3.4×20 cm, eluent: CHCl$_3$/MeOH, 99/1). TLC: Rf, 0.45 (CHCl$_3$/MeOH, 49/1). Yield: 3.27 g (8.53 mmol, 75%).

(4) Synthesis of Ac-DL-Lys(For, OBzl)-OH

TFA (9 mL) was added to Ac-DL-Lys(or, OBzl)-OtBu (3.27 g, 8.53 mmol), and this mixture was left to stand at room temperature for 2 hours. The reaction solution was concentrated and extracted with ethyl acetate. The enact was washed 3 times with water, and dried over magnesium sulfate, and then ethyl acetate was removed by evaporation.

(5) Synthesis of Boc-L-Lys(For, OBzl)-OH

Ac-DL-Lys(For, OBzl)-OH (8.53 mmol) was dissolved in distilled water (2 mL), and the pH of this solution was adjusted to 7 using 2 N aqueous sodium hydroxide solution. Cobalt chloride hexahydrate (7 mg) and *Aspergillus* genus aminoacylase (260 mg) were added to this solution, and the mixture was left to stand overnight at 40° C. The reaction solution was concentrated to 5 mL, and dioxane (5 mL was added. While cooling on ice, Boc$_2$O (1.86 g, 8.52 mmol) and Et$_3$N (1.79 ml, 12.8 mmol) were added to this solution, and the mixture was stirred for 6 hours. Dioxane was removed by evaporation, and the residue was extracted with ethyl acetate. The extract was washed 3 times each with 10% aqueous citric acid solution and water, dried over magnesium sulfate, and then ethyl acetate was removed by evaporation to yield the desired product as an oil. Yield: 2.34 g (6.15 mmol, 100%).

(6) Synthesis of Boc-L-Lys(For, OBzl)-OTmse

Boc-L-Lys(For, OBzl)-OH (2.34 g, 6.15 mmol) and Tmse-OH (1.76 ml, 12.8 mmol) were dissolved in DCM (3 mL). While cooling on ice, DMAP (15 mg, 0.62 mmol) and DCC (1.52 g, 7.38 mmol) were added and the mixture was stirred for 10 hours. The reaction solution was concentrated, and the residue was extracted with ethyl acetate. The extract was washed 3 times each with 10% aqueous citric acid solution, 4% aqueous sodium bicarbonate solution, and saturated brine, and dried over magnesium sulfate, and then ethyl acetate was removed by evaporation. Purification of the residue by silica gel chromatography yielded the desired product as an oil (column: Merck Kieselgel 60 Φ 2.4×20 cm, eluent: AcOEt/hexane, 1/4). TLC: Rf, 0.5 (CHCl$_3$/MeOH, 99/1). Yield: 338 mg (0.7 mmol, 11%).

(7) Synthesis of Boc-L-Ile-DL-Pip-OBzl

Boc-L-Ile-OH.1/2H$_2$O (2.88 g, 12 mmol), HCl.H-DL-Pip-OBzl (2.55 g, 10 mmol), and HOBt.H$_2$O (2.30 g, 15 mmol) were dissolved in DMF (10 mL), and while cooling on ice, Et$_3$N (1.4 ml, 10 mmol) and DCC (3.10 g, 15 mmol) were added. The mixture was stirred overnight, insoluble material was filtered off, and the reaction solution was concentrated. The residue was extracted with ethyl acetate, washed 3 times each with 10% aqueous citric acid solution, 4% aqueous sodium bicarbonate solution, and saturated brine, and dried over magnesium sulfate, and then ethyl acetate was removed by evaporation to yield the desired product as a foam. Yield: 3.79 g (9.1 mmol, 91%).

(8) Synthesis of Boc-D-Tyr(Me)-L-Ile-DL-Pip-OBzl

TFA (4 mL) was added to Boc-L-Ile-DL-Pip-OBzl (2.64 g, 6.1 mmol) under ice-cold conditions, and this was left to stand for 30 minutes. TFA was removed by evaporation, then Boc-D-Tyr(Me)-OH (2.16 g, 7.3 mmol) and HOBt.H$_2$O (1.40 g, 9.15 mmol) were added, and this mixture was dissolved in DMF (10 mL). While cooling on ice, HBTU (3.47 g, 9.15 mmol) and Et$_3$N (3.51 ml, 25 mmol) were added to the solution, and this was stirred for 1 hour. The reaction solution was concentrated, and the residue was extracted with ethyl acetate. The extract was washed 3 times each with 10% aqueous citric acid solution, 4% aqueous sodium bicarbonate solution, and saturated brine, and dried over magnesium sulfate, and then ethyl acetate was removed by evaporation. Purification of the residue by silica gel chromatography yielded the desired product as a foam (column: Merck Kieselgel 60 Φ 5.0×12 cm, eluent: CHCl$_3$/MeOH, 99/1). TLC: Rf, 0.75 (CHCl$_3$/MeOH, 9/1). Yield: 2.45 g (4.02 mmol, 66%).

(9) Synthesis of Boc-D-Tyr(Me)-L-Ile-DL-Pip-OH

Boc-D-Tyr(Me)-L-ILe-DL-Pip-Ozl (2.45 g, 4.02 mmol) was dissolved in methanol (10 mL), Pd—C (500 mg) was added, and this solution was placed under hydrogen atmosphere, and stirred at room temperature for 3 hours. After checking the reaction, Pd—C was filtered off, and methanol was removed by evaporation to yield the desired product as a foam. Yield: 1.98 g (3.81 mmol, 95%).

(10) Synthesis of Boc-D-Tyr(Me)-L-Ile-DL-Pip-L-Lys(For, OBzl)-OTmse

While cooling on ice, TFA (1 mL) was added to Boc-L-Lys(For, OBzl)-OTmse (338 mg, 0.7 mmol), and this was left to stand for 30 minutes. After TFA was removed by evaporation, Boc-D-Tyr(Me)-L-Ile-DL-Pip-OH (363 mg, 0.7 mmol) and HOBt.H$_2$O (160 mg, 1.05 mmol) were added to the residue, and this mixture was dissolved in DMF (1 mL). While cooling on ice, HBTU (398 mg, 1.05 mmol) and Et$_3$N (0.41 ml, 2.9 mmol) were added, and this was stirred for 1 hour. The reaction solution was concentrated, and the residue was extracted with ethyl acetate. The extract was washed 3 times each with 10% aqueous citric acid solution, 4% aqueous sodium bicarbonate solution, and saturated brine, and dried over magnesium sulfate, and then ethyl acetate was removed by evaporation. Purification of the residue by silica gel chromatography yielded the desired product as a foam (column: Merck Kieselgel 60 Φ 1.5×12 cm, eluent: CHCl$_3$/MeOH, 99/1). TLC: Rf, 0.3 (CHCl$_3$/MeOH, 49/1). Yield: 485 mg (0.55 mmol, 79%).

(11) Synthesis of TFA.H-D-Tyr(Me)-L-Ile-DL-Pip-L-Lys (For, OBzl)-OH

Boc-D-Tyr(Me)-L-Ile-DL-Pip-L-Lys(For, OBzl)-OTmse (485 mg, 0.55 mmol) was dissolved in DMF (0.5 mL), and 1 M TBAF/THF (2.2 ml, 2.2 mmol) was added. This was left to stand at room temperature for 30 minutes. The reaction solution was concentrated, a-ad the residue was extracted with ethyl acetate. The extract was washed 3 times each with 10% aqueous citric acid solution and distilled water, and dried over magnesium sulfate, and then ethyl acetate was removed by evaporation. While cooling on ice, TFA (2 mL) was added to this residue and the mixture was left to stand for 30 minutes. After removing TFA by evaporation, addition of diethyl ether and petroleum ether yielded a white powder. Yield: 489 mg (0.55 mmol, 100%).

(12) Synthesis of cyclo(-L-Lys(For, OBzl)-D-Tyr(Me)-L-Ile-L-Pip-) and cyclo(-L-Lys(For, OBzl)-D-Tyr(Me)-L-Ile-D-Pip-)

TFA.H-D-Tyr(Me)-L-Ile-DL-Pip-L-Lys(For, OBzl)-OH (489 mg, 0.55 mmol) was dissolved in DMF (5 mL). This tetrapeptide/DMF solution (1 mL), HATU (63 mg, 0.16 mmol), and 0.076 M DIEA/DMF solution (1 mL) were added to DMF (275 mL), and this was stirred at room temperature for 1 hour. This was repeated 5 times. The reaction solution was concentrated, and the residue was extracted with ethyl acetate. The extract was washed 3 times each with 10% aqueous citric acid solution, 4% aqueous sodium bicarbonate solution, and saturated brine. This was dried over magnesium sulfate, and then ethyl acetate was removed by evaporation. The residue was purified by silica gel chromatography, and the diastereomers (LDLL-form and LDLD-form) were separated. The desired products were obtained separately as foams (column: Merck Kieselgel 60 Φ 1.5×35 cm, eluent: $CHCl_3$/MeOH, 99/1). LDLL-form: Yield 88 mg (0.13 mmol, 24%), TLC: Rf, 0.8 ($CHCl_3$/MeOH, 9/1), RP-HPLC retention time: 22.44 min (column: WakoPak C18 Φ4.6×150 mm, eluent: $CH_3CN$ 10-100%/0.1% TFA linear gradient over 30 min, flow rate: 1 ml/min). LDLD-form: Yield 92 mg (0.14 mmol, 25%), TLC: Rf, 0.9 ($CHCl_3$/MeOH, 9/1), RP-HPLC retention time: 24.59 min (column: WakoPak C18 Φ4.6×150 mm, eluent: $CH_3CN$ 10-100%/0.1% TFA linear gradient over 30 min, flow rate: 1 ml/min).

(13) Synthesis of cyclo(-L-Lys(For, OH)-D-Tyr(Me)-L-Ile-L-Pip-)

Cyclo(-L-Lys(For, OBzl)-D-Tyr(Me)-L-Ile-L-Pip-) (88 mg, 0.13 mmol) was dissolved in methanol (2 mL). Pd—C (100 mg) was then added, and the mixture was stirred under hydrogen atmosphere at room temperature for 1 hour. Pd—C was filtered off, and methanol was removed by evaporation. The residue was freeze-dried to yield a white powder. Yield: 76 mg (0.13 mmol, 100%). RP-HPLC retention time: 17.78 min (column: WakoPak C18 Φ4.6×150 mm, eluent: $CH_3CN$ 10-100%/0.1% TFA linear gradient over 30 min, flow rate: 1 ml/min). FABMS (matrix: 2,2'-dithiodiethanol): m/z, 574.3228 $[M+H]^+$ (Calcd., 573.3163, $C_{29}H_{43}O_7N_5$).

(14) Synthesis of cyclo(-L-Lys(For, OH)-D-Tyr(Me)-L-Ile-D-Pip-)

Cyclo(-L-Lys(For, OBzl)-D-Tyr(Me)-L-Ile-D-Pip-) (92 mg, 0.14 mmol) was dissolved in methanol (2 mL). Pd—C (100 mg) was added, and the mixture was stirred under hydrogen atmosphere at room temperature for 1 hour. After checking the reaction by HPLC, Pd—C was filtered off, and methanol was removed by evaporation. The residue was freeze-dried to yield a white powder. Yield: 75 mg (0.13 mmol, 93%). RP-HPLC retention time: 19.57 min (column: Wako-Pak C18 Φ4.6×150 mm, eluent: $CH_3CN$ 10-100%/0.1% TFA linear gradient over 30 min. flow rate: 1 ml/min). FABMS (matrix: 2,2'-dithiodiethanol): m/z, 574.3230 $[M+H]^+$ (Calcd., 573.3163, $C_{29}H_{43}O_7N_5$).

EXAMPLE 3

Synthesis of cyclo(-L-Hly(For, OH)-D-Tyr(Me)-L-Ile-L-Pip-) and cyclo(-L-Hly(For, OH)-D-Tyr(Me)-L-Ile-D-Pip-)

(1) Synthesis of Boc-L-Ab7-OTmse

Boc-L-Ab7-OH (2.7 g, 8.3 mmol) and Tmse-OH (2.37 ml, 16.6 mmol) were dissolved in DCM (4 mL), and DMAP (101 mg, 0.83 mmol) and DCC (2.05 g, 9.96 mmol) were added while cooling on ice. The mixture was stirred for 6 hours. The reaction solution was concentrated, and extracted with ethyl acetate. The extract was washed 3 times each with 10% aqueous citric acid solution, 4% aqueous sodium bicarbonate solution, and saturated brine, and dried over magnesium sulfate, and then ethyl acetate was removed by evaporation. Purification by silica gel chromatography yielded the desired product as an oil (column: Merck Kieselgel 60 Φ 3.4×20 cm, eluent: AcOEt/hexane, 1/8). TLC: Rf, 0.85 ($CHCl_3$/MeOH, 49/1). Yield: 1.92 mg (4.54 mmol, 55%).

(2) Synthesis of formic O-benzylhydroxamate

O-benzylhydroxylamine hydrochloride (3.19 g, 20 mmol) was dissolved in chloroform, washed with 4% aqueous sodium bicarbonate solution, and dried over sodium carbonate, and chloroform was removed by evaporation. This was dissolved in formic acid (20 mL). Meanwhile, while cooling on ice, acetic anhydride (7.5 mL, 80 mmol) was added to formic acid (40 mL), and the mixture was left to stand for 30 minutes. The formic acid solution of O-benylhydroxylamine was added to this mixture, and the solution was stirred for 24 hours. The reaction solution was concentrated, and the residue was extracted with ethyl acetate. The extract was washed 3 times each with 10% aqueous citric acid solution, 4% aqueous sodium bicarbonate solution, and saturated brine, then dried over sodium carbonate, and ethyl acetate was removed by evaporation. Purification by silica gel chromatography yielded the desired product as a syrup (column: Merck Kieselgel 60 Φ 5.0×12 cm, eluent: AcOEt/hexane, 1/1). TLC: Rf, 0.3 ($CHCl_3$/NeOH, 49/1). Yield: 1.69 g (11.2 mmol, 56%).

(3) Synthesis of Boc-L-Hly(For, OBzl)-OTmse

Boc-L-Ab7-OTmse (846 mg, 2.0 mmol), formic O-benzylhydroxamate (453 mg, 3.0 mmol), potassium iodide (166 mg, 1.0 mmol), and potassium carbonate (1.20 g, 8.0 mmol) were dissolved in dry acetone (40 mL), and the solution was heated under reflux at 90° C. for 4 days. The reaction solution was filtered and then concentrated. The residue was extracted with diethyl ether, washed once with 0.5 N aqueous sodium hydroxide solution, washed twice with distilled water, and then dried over anhydrous sodium carbonate, and diethyl ether was removed by evaporation. Purification by silica gel chromatography yielded the desired product as an oil (column: Merck Kieselgel 60 Φ 2.4×15 cm, eluent: AcOEt/hexane, 1/3). TLC: Rf, 0.5 ($CHCl_3$/MeOH, 49/1). Yield: 235 mg (0.48 mmol, 24%).

(4) Synthesis of Boc-D-Tyr(Me)-L-Ile-DL-Pip-L-Hly(For, OBzl)-OTmse

While cooling on ice, TFA (1 mL) was added to Boc-L-Hly(For, OBzl)-OTmse (235 mg, 0.48 mmol), and this was left to stand for 30 minutes. After removing TFA by evaporation, Boc-D-Tyr(Me)-L-Ile-DL-Pip-OH (233 mg, 0.45 mmol) and $HOBt.H_2O$ (110 mg, 0.72 mmol) were added, and this mixture was dissolved in DMF (1 mL). While cooling on ice, HBTU (273 mg, 0.72 mmol) and $Et_3N$ (0.27 ml, 1.9 mmol) were added, and this was stirred for 1 hour. The reaction solution was concentrated, and the residue was extracted with ethyl acetate. The extract was washed 3 times each with 10% aqueous citric acid solution, 4% aqueous sodium bicarbonate solution, and saturated brine, and dried over magnesium sulfate, and then ethyl acetate was removed by evaporation. Purification by silica gel chromatography yielded the desired product as a foam (column: Merck Kieselgel 60 Φ 2.4×20 cm, eluent: $CHCl_3$/MeOH, 99/1). TLC: Rf, 0.65 ($CHCl_3$/MeOH, 9/1). Yield: 289 mg (0.32 mmol, 71%).

(5) Synthesis of TFA.H-D-Tyr(Me)-L-Ile-DL-Pip-L-Hly (For, OBzl)-OH

Boc-D-Tyr(Me)-L-Ile-DL-Pip-L-Hly(For, OBzl)-OTmse (289 mg, 0.32 mmol) was dissolved in DMF (1 mL), and then 1 M TBAF/THF (0.7 mL, 0.7 mmol) was added. This was left to stand for 30 minutes. The reaction solution was concentrated, and then extacted with ethyl acetate. The extract was washed 3 times each with 10% aqueous citric acid solution and distilled water, and dried over magnesium sulfate, and then ethyl acetate was removed by evaporation. While cooling on ice, TFA (3 mL) was added to this residue, and this mixture was left to stand for 30 minutes. Removal of TFA by evaporation, followed by addition of diethyl ether and petroleum ether yielded a white powder. Yield: 261 mg (0.32 mmol, 100%).

(6) Synthesis of cyclo(-L-Hly(For, OBzl)-D-Tyr(Me)-L-Ile-L-Pip-) and cyclo(-L-Hly(For, OBzl)-D-Tyr(Me)-L-Ile-D-Pip-)

TFA.H-D-Tyr(Me)-L-Ile-DL-Pip-L-Hly(For, OBzl)-OH (261 mg, 0.32 mmol) was dissolved in DMF (3 mL). This tetrapeptide/DMF solution (1 mL), HATU (62 mg, 0.16 mmol), and 0.075 M DIEA/DMF solution (1 mL) were added to DMF (270 mL), and this was stirred at room temperature for 45 minutes. This was repeated 3 times. Then, the reaction solution was concentrated, and the residue was extracted with ethyl acetate. This extract was washed 3 times each with 10% aqueous citric acid solution, 4% aqueous sodium bicarbonate solution, and saturated brine, and dried over magnesium sulfate, and then ethyl acetate was removed by evaporation. The residue was purified by silica gel chromatography, and the diastereomers (LDLL-form and LDLD-form) were separated (column: Merck Kieselgel 60 Φ 1.5×36 cm, eluent: $CHCl_3$/MeOH, 99/1). LDLL-form: Yield 61 mg (0.090 mmol, 28%), TLC: Rf, 0.55 ($CHCl_3$/MeOH, 9/1), RP-HPLC retention time: 22.40 min (column: YMC-Pack C8 Φ4.6×150 mm, eluert: $CH_3CN$ 10-100%/0.1% TFA linear gradient over 30 min, flow rate: 1 ml/min). LDLD-form: Yield 60 mg (0.089 mmol, 28%), TLC: Rf, 0.65 ($CHCl_3$/MeOH, 9/1), RP-HPLC retention time: 24.29 min (column: YMC-Pack C8 Φ4.6×150 mm, eluent: $CH_3CN$ 10-100%/0.1% TFA linear gradient over 30 min, flow rate: 1 ml/min).

(7) Synthesis of cyclo(-L-Hly(For, OH)-D-Tyr(Me)-L-Ile-L-Pip-)

Cyclo(-L-Hly(For, OBzl)-D-Tyr(Me)-L-Ile-L-Pip-) (61 mg, 0.090 mmol) was dissolved in acetic acid (2 mL). Pd—C (100 mg) was added, and the mixture was stirred under hydrogen atmosphere at room temperature for 1 hour. Pd—C was filtered off, and acetic acid was removed by evaporation. Freeze-drying this residue yielded a white powder. Yield: 48 mg (0.082 mmol, 91%). RP-HPLC retention time: 16.02 min (column: WakoPak C18 Φ4.6×150 mm, eluent: $CH_3CN$ 10-100%/0.1% TFA linear gradient over 30 min, flow rate: 1 ml/min). FABMS (matrix: 2,2'-dithodoethanol): m/z, 588.3379 $[M+H]^+$(Calcd., 587.3319, $C_{30}H_{45}O_7N_5$).

(8) Synthesis of cyclo(-L-Hly(For, OH)-D-Tyr(Me)-L-Ile-D-Pip-)

Cyclo(-L-Hly(For, OBzl)-D-Tyr(Me)-L-Ile-D-Pip-) (60 mg, 0.089 mmol) was dissolved in methanol (2 mL), and then Pd—C (100 mg) was added. The mixture was stirred under hydrogen atmosphere at room temperature for 1 hour. Pd—C was filtered off, and methanol was removed by evaporation. Freeze-drying this residue yielded a white powder. Yield: 38 mg (0.065 mmol, 73%). RP-HPLC retention time: 18.68 min (column: WakoPak C18 Φ4.6×150 mm, eluent: $CH_3CN$ 10-100%/0.1% TFA linear gradient over 30 min, flow rate: 1 ml/min). FABMS (matrix: 2,2'-dithiodiethanol): m/z, 588.3388 $[M+H]^+$(Calcd., 587.3319, $C_{30}H_{45}O_7N_5$).

EXAMPLE 4

Synthesis of cyclo(-L-Hly(For, OH)-D-Tyr(Me)-L-Ile-L-Pro-)

(1) Synthesis of Boc-L-Ab7-OTmse

Boc-L-Ab7-OH (1.46 g, 4.5 mmol) and Tmse-OH (0.77 ml, 5.4 mmol) were dissolved in DCM (10 mL), and while cooling on ice, DMAP (55 mg, 0.45 mmol) and DCC (1.1 g, 5.4 mmol) were added. This was then stirred for 16 hours. The solvent was removed by evaporation, and the residue was extracted with ethyl acetate. The extract was washed 3 times each with 10% aqueous citric acid solution, 4% aqueous sodium bicarbonate solution, and saturated brine, and dried over magnesium sulfate, and then ethyl acetate was removed by evaporation. Purification by silica gel chromatography yielded the desired product as an oil (column: Merck Kieselgel 60 Φ 3.4×30 cm, eluent: $CHCl_3$). TLC: Rf, 0.95 ($CHCl_3$/MeOH, 9/1). Yield: 1.25 g (3.0 mmol, 67%).

(2) Synthesis of Boc-L-Hly(For, OBzl)-OTmse

Boc-L-Ab7-OTmse (2.3 g, 5.5 mmol), formic O-benzylhydroxamate (1.45 g, 9.6 mmol), potassium iodide (465 mg, 2.8 mmol), and potassium carbonate (3.04 g, 22 mmol) were dissolved in dry acetone (50 mL), and the solution was heated under reflux at 90° C. for 36 hours. The reaction solution was filtered and then concentrated. The residue was extracted with diethyl ether, washed once with 0.5 N aqueous sodium hydroxide solution, washed twice with distilled water, and then dried over magnesium sulfate, and diethyl ether was removed by evaporation. Purification by silica gel chromatography yielded the desired product as an oil (column: Merck Kieselgel 60 Φ 3.4×30 cm, eluent: $CHCl_3$/MeOH, 49/1). TLC: Rf, 0.4 ($CHCl_3$/MeOH, 49/1). Yield 1.33 g (2.7 mmol, 49%).

(3) Synthesis of Boc-L-Ile-L-Pro-OBzl

Boc-L-Ile-OH.1/2 $H_2O$ (1.19 g, 5.0 mmol) and HCl.H-L-Pro-OBzl (1.02 g, 5.0 mmol) were dissolved in DMF (10 mL), and while cooling on ice, HOBt.$H_2O$ (765 mg, 5.0 mmol), DCC (1.24 g, 6.0 mmol), and $Et_3N$ (0.7 ml, 5.0 mmol) were added, and this mixture was stirred for 16 hours. The solvent was removed by evaporation, and the residue was extracted with ethyl acetate. The extract was washed 3 times each with 10% aqueous citric acid solution, 4% aqueous sodium bicarbonate solution, and saturated brine, and dried over magnesium sulfate, and then ethyl acetate was removed by evaporation. Purification by silica gel chromatography yielded the desired product as an oil (column: Merck Kieselgel 60 Φ 3.4×30 cm, eluent: $CHCl_3$/MeOH, 49/1). TLC: Rf, 0.8 ($CHCl_3$/MeOH, 19/1). Yield: 1.00 g (2.6 mmol, 52%).

(4) Synthesis of Boc-D-Tyr(Me)-L-Ile-L-Pro-OBzl

While cooling on ice, TFA (4 mL) was added to Boc-L-Ile-L-Pro-OBzl (1.00 g, 2.6 mmol), and this was left to stand for 30 minutes. TFA was removed by evaporation, and the residue was dried under reduced pressure. This was dissolved in DMF (6 mL), and Boc-D-Tyr(Me)-OH (770 mg, 2.6 mmol) was added. Then while cooling on ice, HOBt.$H_2O$ (597 mg, 3.9 mmol), HBTU (1.50 g, 3.9 mmol), and $Et_3N$ (0.88 ml, 6.3 mmol) were added, and the mixture was stirred for 16 hours. The reaction solution was concentrated, and extacted with ethyl acetate. The extract was washed 3 times each with 10% aqueous citric acid solution, 4% aqueous sodium bicarbonate solution, and saturated brine, and dried over magnesium sulfate, and then ethyl acetate was removed by evaporation. Purification by silica gel chromatography yielded the desired product as a foam (column: Merck Kieselgel 60 Φ 3.4×30 cm, eluent: CHCl$_3$/MeOH, 99/1). TLC: Rf, 0.45 (CHCl$_3$/MeOH, 19/1). Yield: 1.17 g (2.06 mmol, 79%).

(5) Synthesis of Boc-D-Tyr(Me)-L-Ile-L-Pro-OH

Boc-D-Tyr(Me)-L-Ile-L-Pro-OBzl (595 mg, 1.0 mmol) was dissolved in methanol (10 mL), Pd—C (200 mg) was added, and this mixture was stirred under hydrogen atmosphere for 3 hours. Pd—C was filtered off, and methanol was removed by evaporation to obtain the desired product as a foam. Yield: 380 mg (0.8 mmol, 80%).

(6) Synthesis of Boc-D-Tyr(Me)-L-Ile-L-Pro-L-Hly(For, OBzl)-OTmse

While cooling on ice, TFA (2 mL) was added to Boc-L-Hly(For, OBzl)-OTmse (394 mg, 0.8 mmol) and this was left to stand for 30 minutes. TFA was removed by evaporation, and the residue was dried under reduced pressure. This was then dissolved in DMF (2 mL), and Boc-D-Tyr(Me)-L-Ile-L-Pro-OH (380 mg, 0.8 mmol) was added, While cooling on ice, HOBt.H$_2$O (183 mg, 1.2 mmol), HBTU (461 mg, 1.2 mmol), and Et$_3$N (0.23 ml, 1.6 mmol) were added, and the mixture was stirred for 16 hours. The reaction solution was concentrated, extracted with ethyl acetate, washed 3 times each with 10% aqueous citric acid solution, 4% aqueous sodium bicarbonate solution, and saturated brine, and dried over magnesium sulfate, and then ethyl acetate was removed by evaporation. Purification by silica gel chromatography yielded the desired product as a foam (column: Merck Kieselgel 60 Φ 3.4×30 cm, eluent: CHCl$_3$/MeOH, 99/1). TLC: Rf, 0.6 (CHCl$_3$/MeOH, 19/1). Yield: 470 mg (0.55 mmol, 69%).

(7) Synthesis of TFA.H-D-Tyr(Me)-L-Ile-L-Pro-L-Hly(For, OBzl)-OH

Boc-D-Tyr(Me)-L-Ile-L-Pro-L-Hly(For, OBzl)-OTmse (470 mg, 0.55 mmol) was dissolved in DMF (2 mL), and 1 M TBAF/THF (1.9 mL, 1.9 mmol) was added. The mixture was left to stand at room temperature for 2 hours. The reaction solution was concentrated, extracted with ethyl acetate, washed 3 times each with 10% aqueous citric acid solution and distilled water, and dried over magnesium sulfate, and then ethyl acetate was removed by evaporation. While cooling on ice, TFA (2 mL) was added to this residue, and this mixture was left to stand for 30 minutes. TFA was removed, and then diethyl ether was added to obtain a white powder. Yield. 437 mg (0.55 mmol, 100%).

(8) Synthesis of cyclo(-L-Hly(For, OBzl)-D-Tyr(Me)-L-Ile-L-Pro-)

TFA.H-D-Tyr(Me)-L-Ile-L-Pro-L-Hly(For, OBzl)-OH (437 mg, 0.55 mmol) was dissolved in DMF (5 mL). This tetrapeptide/DMF solution (1 mL), HATU (63 mg, 0.017 mmol) and 0.057 M DIEA/DMF solution (1 mL, 0.33 mmol) were added to DMF (160 mL), and this was stirred at room temperature for 30 minutes. This was repeated 3 times, and then the reaction solution was concentrated. The residue was extracted with ethyl acetate, washed 3 times each with 10% aqueous citric acid solution, 4% aqueous sodium bicarbonate solution, and saturated brine, and dried over magnesium sulfate, and then ethyl acetate was removed by evaporation. Purification by silica gel chromatography yielded a white powder (column: Merck Kieselgel 60 Φ1.5×30 cm, eluent: CHCl$_3$). TLC: Rf, 0.55 (CHCl$_3$/MeOH, 19/1). Yield 160 mg (0.24 mmol, 44%). RP-HPLC retention time: 7.2 min (column: Chromolith performance RP-18e, eluent: CH$_3$CN 10-100%/0.1% TFA linear gradient over 15 min, flow rate: 2 ml/min). HR-FABMS (matrix: 2,2'-dithiodiethanol): m/z, 664.3735 [M+H]$^+$(Calcd., 663.3632, C$_{36}$H$_{50}$O$_7$N$_5$).

(9) Synthesis of cyclo(-L-Hly(For, OH)-D-Tyr(Me)-L-Ile-L-Pro-)

Cyclo(-L-Hly(For, OBzl)-D-Tyr(Me)-L-Ile-L-Pro-) (160 mg, 0.24 mmol) was dissolved in acetic acid (3 mL), and Pd-barium sulfate (100 mg) was added. The mixture was stirred under hydrogen atmosphere at room temperature for 5 hours. Pd-barium sulfate was filtered off, the solvent was removed by evaporation, and crystallization from the residue was carried out using diethyl ether. Yield: 68 mg (0.12 mmol, 50%). RP-HPLC retention time: 6.2 min (column: Chromolith performance RP-18e, eluent: CH$_3$CN 10-100%/0.1% TFA linear gradient over 15 min, flow rate: 2 ml/min). HR-FABMS (matrix: 2,2'-dithiodiethanol): m/z, 574.3259 [M+H]$^+$(Calcd., 573.3163, C$_{29}$H$_{44}$O$_7$N$_5$).

EXAMPLE 5

Synthesis of cyclo(-L-Hly(For, OH)-D-Tyr(Me)-L-Ile-D-Pro-)

(1) Synthesis of Boc-L-Ile-D-Pro-OBzl

Boc-L-Ile-OH.1/2 H$_2$O (1.39 g, 6.0 mmol) and HCl.H-D-Pro-OBzl (956 mg, 4.0 mmol) were dissolved in DMF (10 mL), then while cooling on ice, HOBt.H$_2$O (613 mg, 4.0 mmol), DCC (1.24 g, 6.0 mmol), and Et$_3$N (0.70 ml, 4.0 mmol) were added, and the mixture was stirred, for 8 hours. The reaction solution was concentrated, extracted with ethyl acetate, and the eat was washed 3 times each with 10% aqueous citric acid solution, 4% aqueous sodium bicarbonate solution, and saturated brine, and dried over magnesium sulfate, and then ethyl acetate was removed by evaporation. Purification by silica gel chromatography yielded an oily substance (column: Merck Kieselgel 60 Φ 3.4×30 cm, eluent: CHCl$_3$/MeOH, 99 1). TLC: Rf, 0.92 (CHCl$_3$/MeOH, 9/1). Yield: 1.63 g (3.38 mmol, 85%).

(2) Synthesis of Boc-D-Tyr(Me)-L-Ile-D-Pro-OBzl

While cooling on ice, TFA (5 mL) was added to Boc-L-Ile-D-Pro-OBzl (1.63 g, 3.38 mmol), and this was left to stand for 30 minutes. TFA was removed by evaporation, and the residue was dried under reduced pressure. This was dissolved in DMF (8 mL), Boc-D-Tyr(Me)-OH (1.50 g, 5.07 mmol) was added, and while cooling on ice, HOBt.H$_2$O (518 mg, 3.38 mmol), HBTU (1.92 g, 5.07 mmol), and Et$_3$N (2.37 ml, 16.9 mmol) were added, and this mixture was stirred for 3 hours. The reaction solution was concentrated, extracted with ethyl acetate, the extract was washed 3 times each with 10% aqueous citric acid solution, 4% aqueous sodium bicarbonate solution, and saturated bee, and dried over magnesium sulfate, and then ethyl acetate was removed by evaporation. Purification by silica gel chromatography yielded the desired product as a foam (column: Merck Kieselgel 60 Φ 3.4×30 cm, eluent: CHCl$_3$/MeOH, 99/1). TLC: Rf, 0.89 (CHCl$_3$/MeOH, 9/1). Yield: 1.44 g (2.42 mmol, 72%).

(3) Synthesis of Boc-D-Tyr(Me)-L-Ile-D-Pro-OH

Boc-D-Tyr(Me)-L-Ile-D-Pro-OBzl (1.44 g, 2.42 mmol) was dissolved in methanol (12 mL), and Pd—C (150 mg) was added. The mixture was stirred under hydrogen atmosphere at room temperature for 5 hours. Pd—C was filtered off, methanol was removed by evaporation, and the desired product was obtained as a foam. Yield: 1.21 g (2.4 mmol, 99%).

(4) Synthesis of Boc-D-Tyr(Me)-L-Ile-D-Pro-L-Hly(For, OBzl)-OTmse

While cooling on ice, TFA (5 mL) was added to Boc-L-Hly(For, OBzl)-OTmse (593 mg, 1.2 mmol), and this was left to stand for 30 minutes. TFA was removed by evaporation, and the residue was dried under reduced pressure. This was dissolved in DMF (3 mL), Boc-D-Tyr(Me)-L-Ile-D-Pro-OH (660 mg, 1.3 mmol) was added, and while cooling on ice, HOBt.H$_2$O (230 mmol), HBTU (760 mg, 2.0 mmol), and Et$_3$N (0.56 ml, 4.0 mmol) were added and this was stirred for 16 hours. The reaction solution was concentrated, extracted with ethyl acetate, the extract was washed 3 times each with 10% aqueous citric acid solution, 4% aqueous sodium bicarbonate solution, and saturated brine, and dried over magnesium sulfate, and then ethyl acetate was removed by evaporation. Purification of the residue by silica gel chromatography yielded the desired product as a foam (column: Merck Kieselgel 60 Φ 3.4×30 cm, eluent: CHCl$_3$/MeOH, 99/1). TLC: Rf, 0.7 (CHCl$_3$/MeOH, 9/1). Yield: 830 mg (0.94 mmol, 83%).

(5) Synthesis of TFA.H-D-Tyr(Me)-L-Ile-D-Pro-L-Hly(For, Ozl)-OH

Boc-D-Tyr(Me)-L-Ile-D-Pro-L-Hly(For, OBzl)-OTmse (830 mg, 0.94 mmol) was dissolved in DMF (2 mL), and 1 M TBAF/THF (1.9 ml, 1.9 mmol) was added. This mixture was left to stand at room temperature for 2 hours. The reaction solution was concentrated, extracted with ethyl acetate, and the extract was washed 3 times each with 10% aqueous citric acid solution, and distilled water, and dried over magnesium sulfate. Then, ethyl acetate was removed by evaporation. TFA (2 mL) was added to this residue while cooling on ice, and this was left to stand for 30 minutes. Removal of TFA by evaporation, followed by addition of diethyl ether, yielded a white powder. Yield 437 mg (0.78 mmol, 93%).

(6) Synthesis of cyclo(-L-Hly(For, OBzl)-D-Tyr(Me)-L-Ile-D-Pro-)

TFA.H-D-Tyr(Me)-L-Ile-D-Pro-Hly(For, OBzl)-OH (437 mg, 0.78 mmol) was dissolved in DMF (5 mL). This tetrapeptide/DMF solution (1 mL), HATU (89 mg, 0.23 mmol), and 0.081 M DIEA/DMF solution (1 ml, 0.47 mmol) were added to DMF (160 mL), and this was stirred at room temperature for 30 minutes. The same procedure was repeated 5 times, and then the reaction solution was concentrated. The residue was extracted with ethyl acetate. This extract was washed 3 times each with 10% aqueous citric acid solution, 4% aqueous sodium bicarbonate solution, and saturated brine, and dried over magnesium sulfate, and then ethyl acetate was removed by evaporation. Purification by silica gel chromatography yielded a white powder (column: Merck Kieselgel 60 Φ 1.5×30 cm, eluent: CHCl$_3$). TLC: Rf, 0.65 (CHCl/MeOH, 9/1). Yield 340 mg (0.51 mmol, 66%). RP-HPLC retention time: 8.2 min (column: Chromolith performance RP-18e, eluent: CH$_3$CN 10-100%/0.1% TFA linear gradient over 15 min, flow rate: 2 ml/min). HR-FABMS (matrix: 2,2'-dithiodiethanol): m/z, 664.3700 [M+H]$^+$(Calcd., 663.3632, C$_{36}$H$_{50}$O$_7$N$_5$).

(7) Synthesis of cyclo(-L-Hly(For, OH)-D-Tyr(Me)-L-Ile-D-Pro-)

Cyclo(-L-Hly(For, OBzl)-D-Tyr(Me)-L-Ile-D-Pro-) (200 mg, 0.30 mmol) was dissolved in methanol (3 mL), Pd-barium sulfate (100 mg) was added, and the mixture was stirred under hydrogen atmosphere at room temperature for 15 hours. Pd-barium sulfate catalyst was filtered off, and then the solvent was removed by evaporation. Freeze-drying of the residue yielded a white powder. Yield: 119 mg (0.21 mmol, 70%). RP-HPLC retention time: 7.0 min (column: Chromolith performance RP-18e, eluent: CH$_3$CN 10-100%/0.1% TFA linear gradient over 15 min, flow rate: 2 ml/min). HR-FABMS (matrix: 2,2'-dithiodiethanol): m/z, 574.3229 [M+H]$^+$(Calcd., 573.3163, C$_{29}$H$_{44}$O$_7$N$_5$).

EXAMPLE 6

Synthesis of cyclo(-L-A2oc(For, OH)-D-Tyr(Me)-L-Ile-L-Pip-) and cyclo(-L-A2oc(For, OH)-D-Tyr(Me)-L-Ile-D-Pip-)

(1) Synthesis of Boc-L-Ab8-OTmse

Boc-L-Ab8-OH (3.37 g, 10 mmol) and Tmse-OH (2.86 ml, 20 mmol) were dissolved in DCM (5 mL). DMAP (122 mg, 1.0 mmol) and DCC (2.48 g, 12 mmol) were added while cooling on ice, and this was stirred for 6 hours. The reaction solution was concentrated, and the residue was extracted with ethyl acetate. The extract was washed 3 times each with 10% aqueous citric acid solution, 4% aqueous sodium bicarbonate solution, and saturated brine, and dried over magnesium sulfate, and then ethyl acetate was removed by evaporation. Purification of this residue by silica gel chromatography yielded the desired product as an oil (column: Merck Kieselgel 60 Φ 3.4×15 cm, eluent: AcOEt/hexane, 1/8). TLC: Rf, 0.9 (CHCl$_3$/MeOH, 9/1). Yield: 4.20 mg (9.60 mmol, 96%/).

(2) Synthesis of Boc-L-A2oc(For, OBzl)-OTmse

Boc-L-Ab8-OTmse (2.39 g, 5.50 mmol), formic O-benzylhydroxamate (1.24 g, 8.2 mmol), potassium iodide (456 mg, 2.75 mmol), and potassium carbonate (3.30 g, 22 mmol) were dissolved in dry acetone (110 mL), and the solution was heated under reflux at 90° C. for 6 days. The reaction solution was filtered and then concentrated. The residue was extracted with diethyl ether, washed once with 5 N aqueous sodium hydroxide solution, washed 3 times with distilled water, and then dried over sodium carbonate, and diethyl ether was removed by evaporation. Purification by silica gel chromatography yielded the desired product as an oil (column: Merck Kieselgel 60 Φ 3.4×20 cm, eluent: AcOEt/hexane, 1/4). TLC: Rf, 0.5 (CHCl$_3$/MeOH, 49/1). Yield: 814 mg (1.60 mmol, 29%).

(3) Synthesis of Boc-D-Tyr(Me)-L-Ile-DL-Pip-L-A2oc(For, OBzl)-OTmse

While cooling on ice, TFA (2 mL) was added to Boc-L-A2oc(For, OBzl)-OTmse (487 mg, 0.96 mmol), and this was left to stand for 30 minutes. After removing TFA by evaporation, Boc-D-Tyr(Me)-L-Ile-DL-Pip-OH (841 mg, 1.61 mmol) and HOBt.H$_2$O (230 mg, 1.50 mmol) were added, and this mixture was dissolved in DMF (2 mL). While cooling on ice, BTU (569 mg, 1.50 mmol), and Et$_3$N (0.60 ml, 4.30 mmol) were added, and this was stirred for 1 hour. The reaction solution was concentrated, and the residue was extracted with ethyl acetate. The extract was washed 3 times each with 10% aqueous citric acid solution, 4% aqueous sodium bicarbonate solution, and saturated brine, and dried over magnesium sulfate, and then ethyl acetate was removed by evaporation. Purification by silica gel chromatography yielded the desired product as a foam (column: Merck Kieselgel 60 Φ 2.4×13 cm, eluent: CHCl$_3$/MeOH, 99/1). TLC: Rf, 0.65 (CHCl$_3$/MeOH, 9/1). Yield: 213 mg (0.23 mmol, 24%).

(4) Synthesis of TFA.H-D-Tyr(Me)-L-Ile-DL-Pip-L-A2oc (For, OBzl)-OH

Boc-D-Tyr(Me)-L-Ile-DL-Pip-L-A2oc(For, OBzl)-OTmse (213 mg, 0.23 mmol) was dissolved in DMF (0.5 mL), 1 M TBAF/THF (0.5 ml, 0.5 mmol) was added, and this was left to stand at room temperature for 30 minutes. The reaction solution was concentrated, and then extracted with ethyl acetate. The extract was washed 3 times each with 10% aqueous citric acid solution, and distilled water, and dried over magnesium sulfate, and then ethyl acetate was removed by evaporation. To the remaining oil, TFA (2 mL) was added while cooling on ice, and this was left to stand for 30 minutes. Removal of TFA by evaporation, followed by addition of diethyl ether and petroleum ether, yielded a white powder. Yield: 186 mg (0.23 mmol, 100%).

(5) Synthesis of cyclo(-L-A2oc(For, OBzl)-D-Tyr(Me)-L-Ile-DL-Pip-)

TFA.H-D-Tyr(Me)-L-Ile-DL-Pip-L-A2-oc(For, OBzl)-OH (261 mg, 0.32 mmol) was dissolved in DMF (3 mL). This tetrapeptide/DMF solution (1 mL), HATU (44 mg, 0.12 mmol), and 0.053 M DIEA/DMF solution (1 mL) were added to DMF (200 mL), and this was stirred at room temperature for 40 minutes. This was repeated 3 times, and then the reaction solution was concentrated. The residue was extracted with ethyl acetate, this extract was washed 3 times each with 10% aqueous citric acid solution, 4% aqueous sodium bicarbonate solution, and saturated brine, and dried over magnesium sulfate, and then ethyl acetate was removed by evaporation. Purification by silica gel chromatography yielded the desired product as a foam (column: Merck Kieselgel 60 Φ 1.5×35 cm, eluent: $CHCl_3$/MeOH, 99/1). Yield: 47 mg (0.068 mmol, 21%). LDLL-form: TLC: Rf, 0.6 ($CHCl_3$/MeOH, 9/1), RP-HPLC retention time: 24.02 min (column: WakoPak C18 Φ4.6×150 mm, eluent: $CH_3CN$ 10-100%/0.1% TFA linear gradient over 30 min, flow rate: 1 ml/min). LDLD-form: TLC: Rf, 0.65 ($CHCl_3$/MeOH, 9/1), RP-HPLC retention time: 26.56 min (column: WakoPak C18 Φ4.6×150 mm, eluent: $CH_3CN$ 10-100%/0.1% TFA linear gradient over 30 min, flow rate: 1 ml/min).

(6) Synthesis of cyclo(-L-A2oc(For, OH)-D-Tyr(Me)-L-Ile-L-Pip-) and cyclo(-L-A2oc(For, OH)-D-Tyr(Me)-L-Ile-D-Pip-)

Cyclo(-L-A2oc(For, OBzl)-D-Tyr(Me)-L-Ile-DL-Pip-) (47 mg, 0.068 mmol) was dissolved in acetic acid (1 ml). Pd—C (100 mg) was added, and the mixture was placed under hydrogen atmosphere and stirred at room temperature for 1 hour. Pd—C was filtered of, and acetic acid was removed by evaporation. The diastereomers (LDLL-form and LDLD-form) were separated and purified by HPLC fractionation. The diastereomers individually yielded a white powder upon freeze-drying (column: YMC-Pack C8 Φ 10×250 mm, eluent: $CH_3CN$ 44-53%/0.1% TFA linear gradient over 20 min, flow rate: 3 ml/min). LDLL-form: Yield 10 mg (0.017 mmol, 25%), RP-HPLC retention time: 20.14 min (column: Wako Pak C18 Φ4.6×150 mm, eluent: $CH_3CN$ 10-100%/0.1% TFA linear gradient over 30 min, flow rate: 1 ml/min). HR-FABMS (matrix: 2,2'-dithiodiethanol): m/z, 602.3521 $[M+H]^+$ (Calcd., 601.3476, $C_{31}H_{47}O_7N_5$). LDLD-form: Yield 6 mg (0.010 mmol, 15%), RP-HPLC retention time: 22.43 min (column: WakoPak C18 Φ4.6×150 mm, eluent: $CH_3CN$ 10-100%/0.1% TFA linear gradient over 30 min, flow rate: 1 ml/min). HR-FABMS (matrix: 2,2'-dithiodiethanol): m/z, 602.3526 $[M+H]^+$(Calcd., 601.3476, $C_{31}H_{47}O_7N_5$).

EXAMPLE 7

Synthesis of cyclo(-L-Am6(Tfacet)-D-Tyr(Me)-L-Ile-D-Pro-)

(1) Synthesis of Boc-L-Ab6-OBzl

Boc-L-Ab6-OH (622 mg, 2.0 mmol) and benzyl alcohol (0.26 ml, 2.4 mmol) were dissolved in DCM (8 mL), and then DMAP (24 mg, 0.2 mmol) and DCC (453 mg, 2.2 mmol) were added while cooling on ice. The mixture was stirred overnight. DCM was removed by evaporation, and ethyl acetate was added to the residue. This solution was washed 3 times each with 10% aqueous citric acid solution and 4% aqueous sodium bicarbonate solution, dried over magnesium sulfate, and ethyl acetate was removed by evaporation. The residue was dried in vacuo, and then purified by flash chromatography (column; Merck Kieselgel 60 Φ 2.5×15 cm, eluent: $CHCl_3$/MeOH, 99/1) to obtain a foam. Yield: 626 mg (1.6 mmol, 78%). TLC: Rf, 0.94 ($CHCl_3$/MeOH, 9/1).

(2) Synthesis of Boc-D-Tyr(Me)-L-Ile-D-Pro-L-Ab6-OBzl

TFA (2 mL) was added to Boc-L-Ab6-OBzl (626 mg, 1.6 mmol) on ice, and this was left to stand for 30 minutes at 0° C. to remove the Boc group. After removing TFA by evaporation, the residue, was dried in vacuo to obtain H-L-Ab6-OBzl.TFA in the form of oil. This oil and Boc-D-Tyr(Me)-L-Ile-D-Pro-OH (870 mg, 1.7 mmol) were dissolved in DMF (3 mL), and while cooling on ice, HATU (712 mg, 1.9 mmol) and $Et_3N$ (0.7 ml, 4.8 mmol) were added, and the mixture was stirred for 3 hours. DMF was removed by evaporation, and ethyl acetate was added to the residue. This solution was washed 3 times each with 10% aqueous citric acid solution, and 4% aqueous sodium bicarbonate solution, and dried over magnesium sulfate, and then ethyl acetate was removed by evaporation. Drying in vacuo, and purification by flash chromatography (column: Merck Kieselgel 60 Φ 2.5×20 cm, eluent: $CHCl_3$/MeOH, 99/1) yielded a foam. Yield: 1.1 g (1.4 mmol, 89%). TLC: Rf, 0.92 ($CHCl_3$/MeOH, 9/1).

(3) Synthesis of Boc-D-Tyr(Me)-L-Ile-D-Pro-L-Ab6-OH

Boc-D-Tyr(Me)-L-Ile-D-Pro-L-Ab6-OBzl (1.1 g, 1.4 mmol) was dissolved in methanol, 5% Pd—C (80 mg) was added, and the mixture was reacted with $H_2$ gas for 6 hours. Removal of methanol by evaporation, and drying in vacuo yielded a foam. Yield: 925 mg (1.3 mmol; 96%). TLC: Rf, 0.52 ($CHCl_3$/MeOH, 9/1).

(4) Synthesis of cyclo(-L-Ab6-D-Tyr(Me)-L-Ile-D-Pro-)

TFA (3 mL) was added to Boc-D-Tyr(Me)-L-Ile-D-Pro-L-Ab6-OH (925 mg, 1.3 mmol) on ice, and this was left to stand for 30 minutes at 0° C. to remove the Boc group. Removal of TFA, and addition of ether-petroleum ether gave a white powder. H-D-Tyr(Me)-L-Ile-D-Pro-L-Ab6-OH.TFA, HBTU (759 mg, 2.0 mmol), HOBt (306 mg, 2.0 mmol), and DIEA (1.46 ml) were divided into 5 portions, and each portion was added every 30 minutes to DMF (240 mL) to carry out a cyclization reaction Two hours later, the solvent was removed by evaporation, and the residue was taken up in ethyl acetate. This solution was washed 3 times with 10% aqueous citric acid solution, 4% aqueous sodium bicarbonate solution, and brine, and dried over magnesium sulfate. Removal of ethyl acetate by evaporation, and purification of the residual oil through a silica gel column yielded a foam. Yield: 267 mg (0.43 mmol, 32%). TLC: Rf, 0.82 ($CHCl_3$/MeOH, 9/1). RP-HPLC retention time, 9.04 min. HR-FABMS (matrix: 2,2'-dithiodiethanol): m/z, 579.2197 $[M+H]^+$, (Calcd., 578.2132, $C_{27}H_{40}O_5N_4S^{79}Br$).

(5) Synthesis of cyclo(-L-Am6(Ac)-D-Tyr(Me)-L-Ile-D-Pro-)

To a solution of cyclo(-L-Ab6-D-Tyr(Me)-L-Ile-D-Pro-) (230 mg, 0.40 mmol) in DMF (1.0 mL) was added potassium thioacetate (69 mg, 0.60 mmol), and this mixture was allowed to react for 3 hours. DMF was removed by evaporation, and the residue was extracted with ethyl acetate. The extract was washed 3 times each with 10% aqueous citric acid solution and saturated brine, and dried over magnesium sulfate. Ethyl acetate was removed by evaporation to obtain a foam. Yield: 230 mg (>100%). TLC: Rf, 0.82 (CHCl$_3$/MeOH, 9/1).

(6) Synthesis of cyclo(-L-Am6(Tfacet)-D-Tyr(Me)-L-Ile-D-Pro-)

Methanolic ammonia (1.0 mL) was reacted with a solution of cyclo(-L-Am6(Ac)-D-Tyr(Me)-L-Ile-D-Pro-) (114 mg, 0.20 mmol) in DMF (1 ml) to remove the acetyl group. After removing the solvent by evaporation, this was dissolved in DMF (1.5 mL). 3-Bromo-1.1.1-trifluoroacetone (0.062 ml, 0.60 mmol) and Et$_3$N (0.085 ml, 0.60 mmol) were then added, and the mixture was allowed to react overnight. DMF was removed by evaporation, the residue was extracted with ethyl acetate, and the extract was washed 3 times each with 10% aqueous citric acid solution and brine, and was dried over magnesium sulfate. Ethyl acetate was removed by evaporation, and purification of the remaining oil by HPLC yielded a white powder (15 mg, 12%). HR-FABMS (matrix: 2,2'-dithiodiethanol); m/z, 643.2768 [M+H]$^+$, (Calcd., 642.2707, C$_{30}$H$_{42}$O$_6$N$_4$F$_3$S).

EXAMPLE 8

Synthesis of cyclo(-L-Tfm-D-Tyr(Me)-L-Ile-D-Pro-)

(1) Synthesis of cyclo(-L-Asu(O—.Li$^+$)-D-Tyr(Me)-L-Ile-D-Pro-)

Cyclo(-L-Asu(OBzl)-D-Tyr(Me)-L-Ile-D-Pro-) (410 mg, 0.63 mmol) together with LiOH (53 mg, 1.2 mmol) were dissolved in THF (2 mL) and water (2 mL), and this solution was stirred at ice-cold temperature overnight. The solvent was removed by evaporation and ether was added for precipitation. Yield: 355 mg (100%). HPLC: 9.7 min (Chromolith, 10-100% CH$_3$CN gradient containing 0.1% TFA over 15 min).

(2) Synthesis of cyclo(-L-Tfm-D-Tyr(Me)-L-Ile-D-Pro-)

Cyclo(-L-Asu(O—.Li+)-D-Tyr(Me)-L-Ile-D-Pro-) (355 mg, 0.63 mmol) was dissolved in CH$_2$Cl$_2$ (10 ml), and (CF$_3$CO)$_2$O (0.6 ml, 3.8 mmol) was added at ice-cold temperature. Then, pyridine (0.41 mL, 5 mmol) was added and the mixture was stirred at room temperature for 4 hours. After shaking the reaction solution with water (10 mL), the desired compound was extracted into CH$_2$Cl$_2$. The organic layer was dried over magnesium sulfate, concentrated by evaporation, and the desired compound was separated and purified from the residue by HPLC. Yield: 155 mg (40%). HPLC: 8.0 min (Chromolith, 10-100% CH$_3$CN gradient containing 0.1% TFA over 15 min). HR-FABMS (matrix: 2,2'-dithiodiethanol): m/z, 611.3041 [M+H]$^+$(Calcd., 610.2966, C$_{30}$H$_{42}$O$_6$F$_3$).

EXAMPLE 9

Synthesis of cyclo(-L-Pfe-D-Tyr(Me)-L-Ile-D-Pro-)

Cyclo(-L-Asu(O—.Li$^+$)-D-Tyr(Me)-L-Ile-D-Pro-) (355 mg, 0.63 mmol) was dissolved in CH$_2$Cl$_2$ (10 ml), and (CF$_3$CF$_2$CO)$_2$O (0.75 ml, 3.8 mmol) was added at ice-cold temperature. Then, pyridine (0.41 mL, 5 mmol) was added, and the mixture was stirred at room temperature for 4 hours. After shaking the reaction solution with water (10 mL), the desired compound was extracted into CH$_2$Cl$_2$. The organic layer was dried over magnesium sulfate, concentrated by evaporation, and the desired compound was separated and purified from the residue by HPLC. Yield: 16 mg (5%). HPLC: 8.8 min (hydrate) and 10.5 (keto) (Chromolith, 10-100% CH$_3$CN gradient containing 0.1% TFA over 15 min). HR-FABMS (matrix: 2,2'-dithiodiethanol): m/z, 661.3050 [M+H]$^+$(Calcd., 660.2955, C$_{31}$H$_{42}$F$_5$O$_6$N$_4$).

EXAMPLE 10

Synthesis of cyclo(-L-Aph-D-Tyr(Me)-L-Ile-D-Pro-)

(1) Synthesis of Boc-L-Aph-OTmse

To a solution of Boc-L-Ab7-OTmse (425 mg, 1 mmol) in acetonitrile (2 mL), NaI (150 mg, 1 mmol) and P(OMe)$_3$ (500 mg, 4 mmol) were added, and this mixture was stirred at 70° C. for 20 hours. Acetonitrile was removed by evaporation, and the residue was extracted with ethyl acetate, washed with water, and then dried over magnesium sulfate. Removal of ethyl acetate by evaporation yielded Boc-L-Aph-OTmse (440 mg, 98%). FABMS (matrix: 2,2'-dithiodiethanol): m/z, 354 [M+H]$^+$.

(2) Synthesis of Boc-L-Aph-OH

To a solution of Boc-L-Aph-OTmse (440 mg, 1 mmol) in DMF (1 ml), 1 M TBAF/THF (2 ml) was added, and this was stirred at room temperature for 2 hours. After removing DMF by evaporation, the residue was dissolved in ethyl acetate, washed with 10% aqueous citric acid solution and brine, and dried over magnesium sulfate. Removal of ethyl acetate by evaporation yielded Boc-L-Aph-OH (250 mg, 0.71 mmol, 70%).

(3) Synthesis of Boc-L-Aph-D-Tyr(Me)-L-Ile-D-Pro-OBzl

Treatment of Boc-D-Tyr(Me)-L-Ile-D-Pro-OBzl (416 mg, 0.7 mmol) with TFA (3 mL) for 30 minutes, followed by removal of TFA by evaporation yielded TFA.H-D-Tyr(Me)-L-Ile-D-Pro-OBzl. A solution of Boc-L-Aph-OH (250 mg, 0.71 mmol) in DMF (3 mL), HBTU (400 mg, 1.05 mmol), HOBt (107 mg, 0.7 mmol), and Et$_3$N (0.5 ml, 3.5 mmol) were added to this product, and the mixture was stirred overnight at 0° C. DMF was removed by evaporation, the residue was extracted with ethyl acetate, and the extract was washed 3 times each with 10% aqueous citric acid solution, 4% aqueous NaHCO$_3$ solution, and saturated brine, and then dried over magnesium sulfate. Removal of ethyl acetate by evaporation, and purification by column chromatography yielded Boc-L-Aph-D-Tyr(Me)-L-Ile-D-Pro-OBzl (200 mg, 0.24 mmol, 35%). MALDI-TOFMS: m/z, 854 [M+Na]$^+$.

(4) Synthesis of cyclo(-L-Aph-D-Tyr(Me)-L-Ile-D-Pro-)

Boc-L-Aph-D-Tyr(Me)-L-Ile-D-Pro-OBzl (200 mg, 0.24 mmol) was hydrogenated in methanol in the presence of 5% Pd/C (50 mg) to obtain Boc-L-Aph-D-Tyr(Me)-L-Ile-D-Pro-OH (160 mg, 0.22 mmol, 92%). The Boc group was removed by a 30-minute TFA (2 mL) treatment while cooling on ice, and TFA removal by evaporation was followed by precipitation with ether. To a solution of the obtained tetrapeptide TFA salt (140 mg, 0.20 mmol) in DMF (75 mL), HATU (114 mg, 0.3 mmol) and DIEA (0.12 ml, 0.7 mmol) were added, and the mixture was stirred at room temperature. Three hours later, DMF was removed under reduced pressure, the residue was extacted with ethyl acetate, and the extract was washed 3 times each with 10% aqueous citric acid solution, 4% aqueous NaHCO$_3$ solution, and saturated brine, and then dried over magnesium sulfate. Ethyl acetate was removed by evaporation, and the remaining oil was purified by column chromatography to obtain the desired product (15 mg, 0.024 mmol, 11%). HPLC retention time, 7.0 min (Chromolith, 10-100% CH$_3$CN gradient containing 0.1% TFA over 15 min). HR-FABMS (matrix: 2,2'-dithiodiethanol): m/z, 623.3177 [M+H]$^+$(Calcd, 623.3210, C$_{30}$H$_{47}$O$_8$N$_4$P).

EXAMPLE 11

Measurement of HDAC Inhibitory Activity

In this Example, compounds with the cyclic tetrapeptide structures and various functional groups for substituent X, i.e., N(OH)COH(n=4), N(OH)COH(n=5), N(OH)COH (n=6), COOH, COOMe, COOBzl, Tfk, Pfek, Mtfk, Stfk, SMe, $SO_2Me$, or Aph, were examined for their enzyme inhibitory activity.

Figure 2:
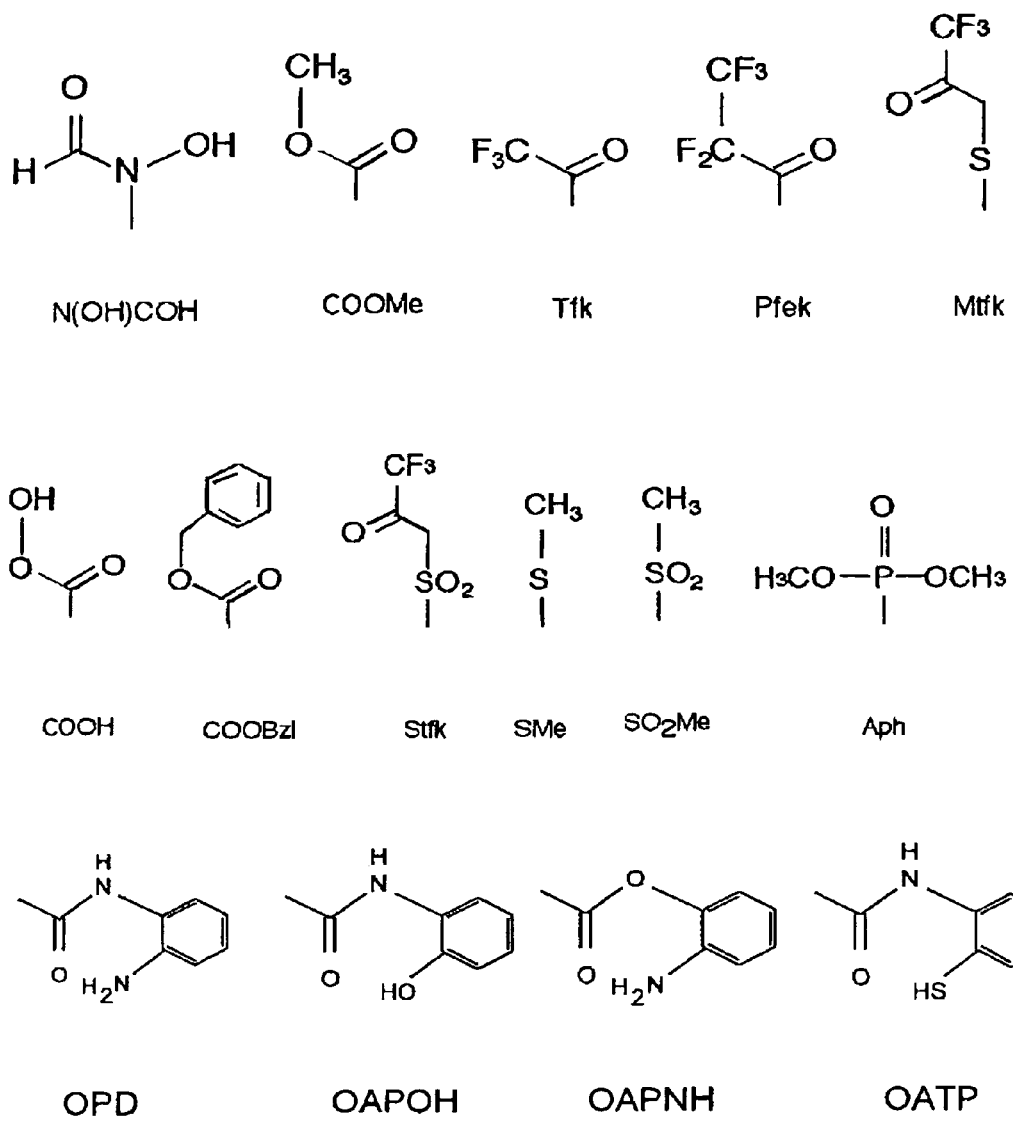
FIG. 2 depicts representative examples of substituent X for inclusion in the compounds of formula (1).
Figure 3:
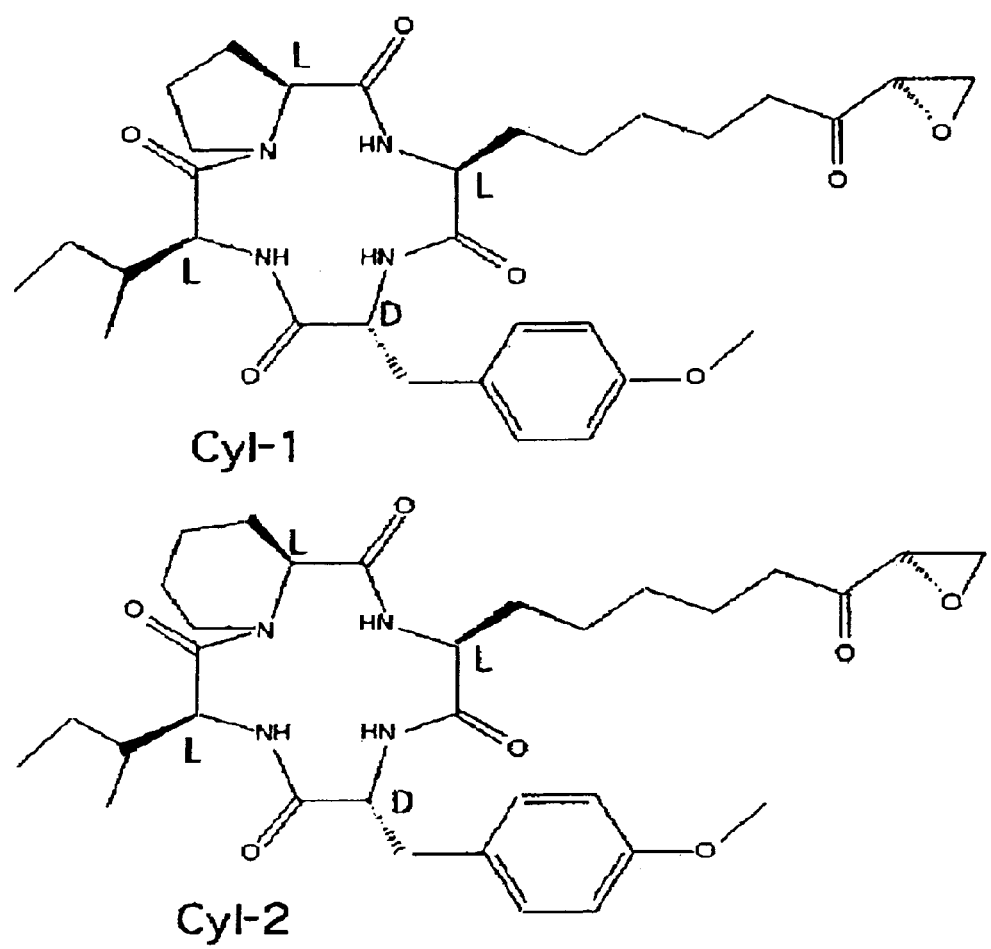
FIG. 3 depicts the three-dimensional confirmations of natural Cyl-1 and Cyl-2.

Structures of the substituents of the compounds used for activity measurements are listed in FIG. 2. Based on natural HDAC inhibitors, such as Cyl-1 and Cyl-2 shown in FIG. 3 (Furumai et al. (2001) Proc. Natl. Acad. Sci. USA, 98, 87-92.), the conformation of the cyclic tetrapeptide and the distance to the active site in terms of carbon chain length were examined. Natural Cyl-1 and Cyl-2 both have the LDLL conformation; however, in this Example, both LDLL-form and LDLD-form compounds were examined.

To measure HDAC inhibitory activity, an HDAC solution was prepared as described below. $1 \times 10^7$ of 293T cells were plated on to a 100-mm dish and, after 24 hours, transfected with vectors (1 µg) expressing human HDAC1 and HDAC4 or mouse HDAC6, using LipofectAmine 2000 reagent (Life Technologies, Inc. Gaithersburg, Md.). pcDNA3-HD1 was used as a vector expressing human HDAC1 (Yang, W. M., Yao, Y. L., Sun, J. M., Davie, J. R. & Seto, E. (1997) J. Biol. Chem. 272, 28001-28007). pcDNA3.1(+)-HD4 was used as a vector expressing human HDAC4 (Fischle, W., Emiliani, S., Hendzel, M. J., Nagase, T., Nomura, N., Voelter, W. & Verdin, E. (1999) J. Biol. Chem. 274, 11713-11720). pcDNA-mHDA2/HDAC6 was used as a vector expressing mouse HDAC6 (Verdel, A. & Khochbin, S. (1999) J. Biol. Chem. 274, 2440-2445).

The vectors were introduced for five hours in OPTI-MEM. The medium was then replaced with Dulbecco's modified Eagle's medium (DMEM), and incubated for 19 hours. The cells were washed with PBS, suspended in lysis buffer (50 mM Tris-HCl (pH7.5), 120 mM NaCl, 5 mM EDTA, and 0.5%, Nonidet P-40), and sonicated. The supernatant was collected by centrifugation and nonspecific protein was removed using Protein A/G plus agarose beads (Santa Cruz Biotechnologies, Inc.). Anti-FLAG M2 antibodies (Sigma-Aldrich, Inc.) were added to the supernatant of cells expressing HDAC1 or HDAC4. Anti-HA antibodies (clone 3F10, Roche Molecular Biochemicals) were added to the supernatant of cells expressing HDAC6. Reaction in the respective mixtures was carried out at 4° C. for one hour.

The resulting reaction mixtures were independently mixed with agarose beads and further reacted at 4° C. for one hour. The agarose beads were washed three times with lysis buffer and then washed once with HD buffer (20 mM Tris-HCl (pH8.0), 150 mM NaCl, 10% glycerol, and a complete protease inhibitor cocktail (Boehringer Mannheim, Germany)). The protein solution, referred to as "HDAC reaction solution", that had bonded to the agarose beads was recovered by incubation with FLAG peptide (40 µg) (Sigma-Aldrich, Inc.) or HA peptide (100 µg) in an HD buffer (200 µl) at 4° C. for one hour. The HDAC reaction solution was used for determining HDAC inhibitory activity as shown below.

HDAC inhibitory activity in an in vitro system was evaluated as follows. The test compound was dissolved in DMSO to prepare a 10 mM stock solution, and this was used as an inhibitor stock solution. Assays were carried out by incubating the HDAC solution and coumarin-labeled acetylated histone peptide solution in the presence of the test compound at 37° C. for 30 minutes (reaction volume 20 µL). Aminomethylcoumarin released by the enzyme reaction, due to addition of 30 µL of trypsin to the reaction solution, was measured using a fluorescence plate reader. For the negative control, the same procedure was performed without adding the inhibitor to the reaction system. Inhibitory activity was expressed as the concentration of test compound that produces 50% inhibition of HDAC activity observed in the negative control, "$IC_{50}$ (µM)" (Table 1).

The HDAC inhibitory activity in vivo was measured using p21 promoter-inducing activity as an index, as shown below. The MFLL-9 cells employed for the experiments stably maintained fusion genes of human wild-type p21 promoter and luciferase (Dr. B. Vogelstaein). Using phenol red-free DMEM medium comprising 10% FBS, cultivation was carried out in a steam-saturated incubator at 37° C. with 5% carbon dioxide. The MFLL-9 cells were plated at a density of 85,000 cells/well on a 96-well microtiter plate, each in 99 µl of the above-mentioned medium. These were then cultivated for six hours. One µl of test compound solution was added to each well, which was then cultured for another 18 hours. TSA was used as the positive control compound with p21 promoter-inducing activity, which results from HDAC inhibitory activity.

The intensity of luminescence caused by the product of the enzyme reaction for intracellular luciferase expression was measured using Luc Lite (Packard BioScience Company). The test compound activity intensities were compared using the concentrations ("$EC_{50}$ (µM)") corresponding to 50% of the maximum active values for TSA (Table 1).

TABLE 1

| | IC50 (µM) | | | P21 PROMOTER | |
|---|---|---|---|---|---|
| X | HDAC1 | HDAC4 | HDAC6 | EC50 (µM) | STRUCTURE |
| N(OH)COH | 33.9 | 25.2 | 14.3 | >100 | Cyclo(X-y(Me)-I-pip), n = 4 |
| N(OH)COH | 23.9 | 17.5 | 8.19 | >100 | Cyclo(X-y(Me)-I-Pip), n = 4 |
| N(OH)COH | 0.067 | 0.13 | 0.18 | 3.73 | Cyclo(X-y(Me)-I-pip), n = 5 |
| N(OH)COH | 6.36 | 7.02 | 12.2 | >100 | Cyclo(X-y(Me)-I-pip), n = 6 |
| N(OH)COH | 13.5 | 18.9 | 11.2 | >100 | Cyclo(X-y(Me)-I-Pip), n = 6 |
| N(OH)COH | 0.026 | 0.074 | 0.78 | 5.42 | Cyclo(X-y(Me)-I-p), n = 5 |
| N(OH)COH | 0.033 | 0.090 | 0.029 | 61.1 | Cyclo(X-y(Me)-I-P), n = 5 |

TABLE 1-continued

| X | IC50 (µM) | | | P21 PROMOTER EC50 (µM) | STRUCTURE |
|---|---|---|---|---|---|
| | HDAC1 | HDAC4 | HDAC6 | | |
| COOH | 4.07 | 5.69 | >500 | >100 | Cyclo(X-y(Me)-I-p), n = 5 |
| COOMe | 0.12 | 0.07 | >500 | 3.95 | Cyclo(X-y(Me)-I-p), n = 5 |
| COOBzl | NT | NT | NT | >100 | Cyclo(X-y(Me)-I-p), n = 5 |
| Tfk | 0.73 | 0.61 | 1.44 | 3.09 | Cyclo(X-y(Me)-I-p), n = 5 |
| Pfek | 0.85 | 1.22 | 5.72 | >100 | Cyclo(X-y(Me)-I-p), n = 5 |
| Mtfk | 0.047 | 0.19 | 0.95 | 6.64 | Cyclo(X-y(Me)-I-p), n = 5 |
| Stfk | >500 | NT | NT | >100 | Cyclo(X-y(Me)-I-p), n = 5 |
| SMe | >500 | >500 | >500 | >100 | Cyclo(X-y(Me)-I-p), n = 5 |
| $SO_2Me$ | >500 | >500 | >500 | >100 | Cyclo(X-y(Me)-I-p), n = 5 |
| Aph | >500 | >500 | >500 | >100 | Cyclo(X-y(Me)-I-p), n = 5 |
| TSA | 0.022 | 0.020 | 0.028 | 0.77 | |

In the Table, y(Me) denotes D-Tyr(Me), Tyr(Me) denotes O-methyltyrosine, I denotes L-Ile, pip denotes D-pipecolic acid, and Pip denotes L-pipecolic acid (the amino acids are indicated by one-letter codes, capital letters indicate L-form amino acids, and lower case letters indicate D-form amino acids). NT stands for Not Tested.

The above results demonstrate that compounds with different X structures have very different inhibitory activities against each of the enzyme subtypes, that is, enzyme subtype selective inhibitory activity.

The compounds of the present invention showed strong inhibitory activity against HDAC1, 4, and 6. Compounds having a cyclic tetrapeptide structure had previously been considered to be unable to inhibit HDAC6; however, by modifying the structure of the tetrapeptide skeleton as in the present invention, conferring inhibitory ability against HDAC6 became possible. Those compounds having different X structures showed very different inhibitory activities against each of the enzyme subtypes, and the compounds of the present invention were shown to have enzyme subtype selective inhibitory activity.

Since the methods for producing the compounds of the present invention facilitate structural modifications of the tetrapeptide skeleton, they are expected to facilitate modification of the selectivity of the compounds towards target enzymes.

EXAMPLE 12

Measurement of HDAC Inhibitory Activity at the Cellular Level

Figure 4:
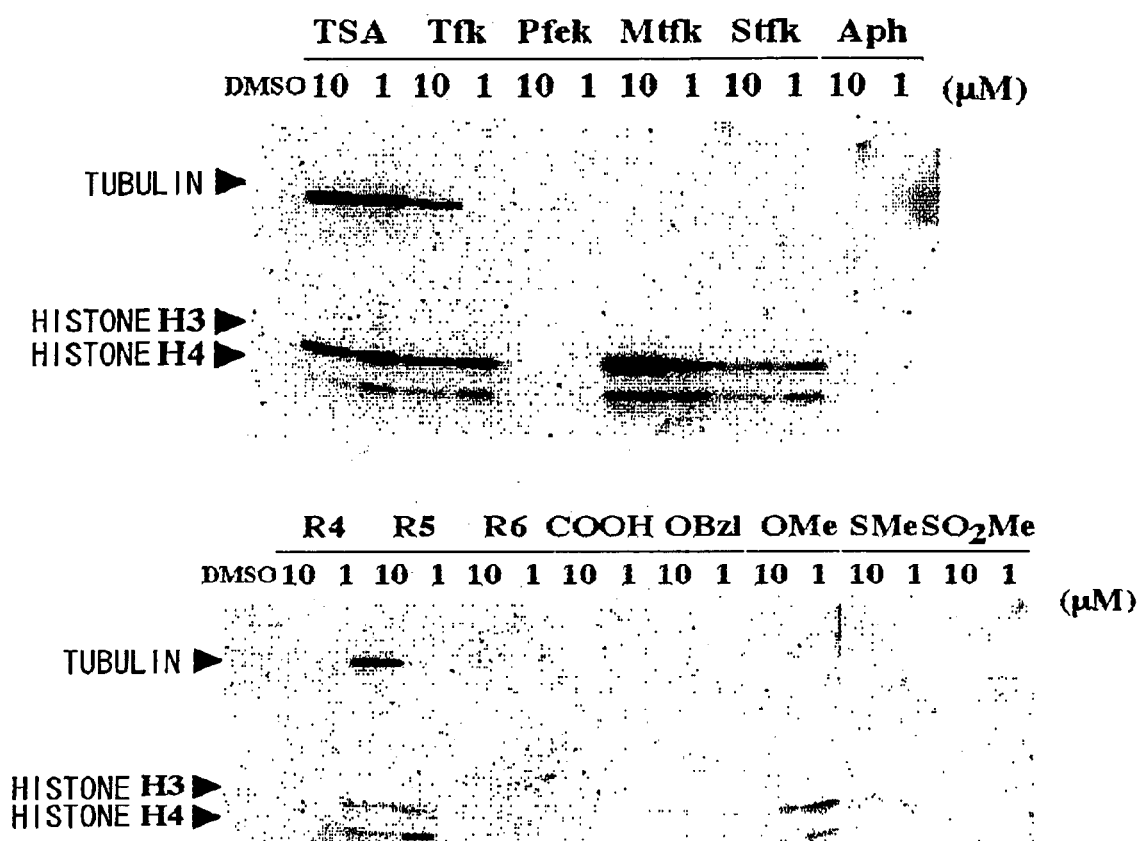
FIG. 4 is a set of photographs depicting the results of measuring the level of tubulin and histone acetylation in cells by western blotting using anti-acetylated lysine antibody. In the Figure, R4, R5, and R6 refer to N(OH)COH(n=4), N(OH)COH(n=5), and N(OH)COH(n=6), respectively.

Tubulin and histone acetylation levels were measured by: (a) reacting a test compound with HeLa cells; and (b) confirming the tubulin and histone acetylation level by western blotting using anti-acetylated lysine antibodies. Specifically, human uterine cancer cells (HeLa) were cultured in a DMEM medium supplemented with 10% FBS at 37° C. in the presence of 5% carbon dioxide in a steam-saturated incubator. Two ml of the cells at a density of 15,000 cells/ml were plated onto a 6-well plate and cultured for 18 hours. Test compound solution was added to each culture and successively cultured for another six hours. The cells were washed with PBS, suspended in a lysis buffer (50 mM Tris-HCl (pH7.5), 120 mM NaCl, 5 mM EDTA, 0.5% Nonidet P-40), and then sonicated. The supernatant was collected by centrifugation, mixed with SDS bufer, and left at 100° C. for five minutes. The resulting sample was subjected to electroplioresis on a 15% SDS gel and transferred to a membrane film. This was treated with primary antibody "AKL5C1" (Japan Energy), and secondary antibody "anti-mouse" (LIFE SCIENCE), and then acetylation bands were detected by ECL (amersham pharmacia biotech) (FIG. 4). The concentration unit of the compounds shown in FIG. 4 is "µM".

As shown in FIG. 4, the compounds showed inhibitory activities consistent with the p21 promoter-inducing activity ($EC_{50}$). Tfk and N(OH)COH(n=5) inhibited tubulin deacetylase in the cells, and induced high level of tubulin acetylation. Such enzyme selectivity is a characteristic not found in other HDAC inhibitors having a cyclic tetrapeptide structure.

EXAMPLE 13

Cytotoxicity Test

Tfk, Pfek, Mtfk, and Aph were tested for their cytotoxicity using normal human lung cells (TIG-3) and human uterine cancer cells (HeLa). Using DMEM medium supplemented with 10% FBS, TIG-3 cells and HeLa cells were cultured in a humidity-saturated incubator at 37° C. under 5% carbon dioxide atmosphere. TIG-3 and HeLa were plated at a cell density of 15,000 cells/well and 5,000 cells/well, respectively, onto a 96-well microplate, and cultured in 100 µL of the above-described medium per well for 18 hours. Then, a test compound solution diluted with the medium was added, and culturing was continued for another 48 hours.

A substrate mixture solution of Cell Proliferation Kit II (XTT) (Roche Diagnostics) was added to each well at 50 µL/well, and this mixture was incubated for a sufficient length of time for color reaction. When the color reaction had progressed sufficiently, the color intensity was measured at OD495 nm using a microplate reader. Inhibitory activity was expressed in terms of $IC_{50}$, which refers to the concentration at which the percentage of free XTT is 50%. Higher values of cancer cell-selective cytotoxicity (IC$_{50}$ of normal TIG cells /IC$_{50}$ of HeLa cancer cells) indicate that more selective cancer cell death was induced.

TABLE 2

| INHIBITOR | IC$_{50}$ (nM) | | CANCER CELL SELECTIVE CYTOTOXICITY |
|---|---|---|---|
| | HeLa | TIG-3 | |
| TSA | 12.3 | 151 | 12.3 |
| Tfk | 8.8 | 87.1 | 9.9 |
| Pfek | 616 | 13443 | 21.8 |
| Mtfk | 52.5 | 468 | 8.9 |
| Aph | >50000 | >50000 | — |

As indicated in Table 2, the compounds of the present invention showed strong cancer cell-specific cytotoxicity similar to that of TSA.

EXAMPLE 14

Synthesis of cyclo(L-Asu(OPD)-D-Tyr(Me)-L-Ile-D-Pro)

(1) Synthesis of cyclo(L-Asu-D-Tyr(Me)-L-Ile-D-Pro)

Cyclo(L-Asu(OBzl)-D-Tyr(Me)-L-Ile-D-Pro) (360 mg, 0.56 mmol) synthesized by existing methods was dissolved in methanol (20 mL), and subjected to catalytic hydrogenation for 5 hours by adding Pd/C (100 mg). Removal of the catalyst by filtration, and methanol by evaporation yielded cyclo(L-Asu-D-Tyr(Me)-L-Ile-D-Pro). Yield 310 mg (0.56 mmol, 100%).

(2) Synthesis of cyclo(L-Asu(OPD)-D-Tyr(Me)-L-Ile-D-Pro)

Cyclo(L-Asu-D-Tyr(Me)-L-Ile-D-Pro) (150 mg, 0.27 mmol) was dissolved in DMF (2 mL), then HOBt.H$_2$O (41 mg, 0.27 mmol), HBTU (154 mg, 0.4 mmol), o-phenylenediamine (58 mg, 0.54 mmol), and triethylamine (0.12 ml, 0.8 mmol) were added at 0° C., and this mixture was stirred for 3 hours. Purification by gel filtration chromatography yielded cyclo(L-Asu(OPD)-D-Tyr(Me)-L-Ile-D-Pro) (column: Sephadex LH-20 Φ 2.0×100 cm, eluent: DMF). Yield: 140 mg (0.216 mmol, 80%).

EXAMPLE 15

Synthesis of cyclo(L-Asu(OAPOH)-D-Tyr(Me)-L-Ile-D-Pro) and cyclo(L-Asu(OAPNH)-D-Tyr(Me)-L-Ile-D-Pro)

Cyclo(L-Asu-D-Tyr(Me)-L-Ile-D-Pro) (150 mg, 0.27 mmol) synthesized by the same method as in Example 1 was dissolved in DMF (2 mL), then HOBt.H$_2$O (41 mg, 0.27 mmol), BOP reagent (179 mg, 0.4 mmol), o-aminophenol (35 mg, 0.32 mmol), and triethylamine (0.12 ml, 0.8 mmol) were added at 0° C., and this i e was stirred for 3 hours. Purification by gel filtration chromatography first yielded cyclo(L-Asu (OAPOH)-D-Tyr(Me)-L-Ile-D-Pro) (column: Sephadex LH-20 Φ 2.0×100 cm, eluent: DMF). Yield; 70 mg (0.108 mmol, 40%). Further elution gave cyclo(L-Asu(OAPNH)-D-Tyr(Me)-L-Ile-D-Pro) (column: Sephadex LH-20 Φ 2.0×100 cm, eluent: DMF). Yield: 50 mg (0.08 mmol, 30%).

EXAMPLE 16

Synthesis of cyclo(L-Asu(OATP)-D-Tyr(Me)-L-Ile-D-Pro) dimer

Cyclo(L-Asu-D-Tyr(Me)-L-Ile-D-Pro) (125 mg, 0.22 mmol) synthesized by the same method as in Example 1 was dissolved in DMF (2 mL), then HOBt.H$_2$O (34 mg, 0.22 mmol), BOP reagent (146 mg, 0.33 mmol), o-aminothiophenol (33 mg, 0.33 mmol), and triethylamine (0.12 ml, 0.8 mmol) were added at 0° C., and this mixture was stirred for 3 hours. Purification by gel filtration chromatography yielded the SS-dimer of cyclo(L-Asu(OATP)-D-Tyr(Me)-L-Ile-D-Pro) (column: Sephadex LH-20 Φ 2.0×100 cm, eluent: DMF). Yield: 120 mg (0.09 mmol, 80%). Reduction of this SS-dimer using dithiothreitol readily gave the HS-form.

EXAMPLE 17

Measurement of HDAC Inhibitory Activity

Figure 5:
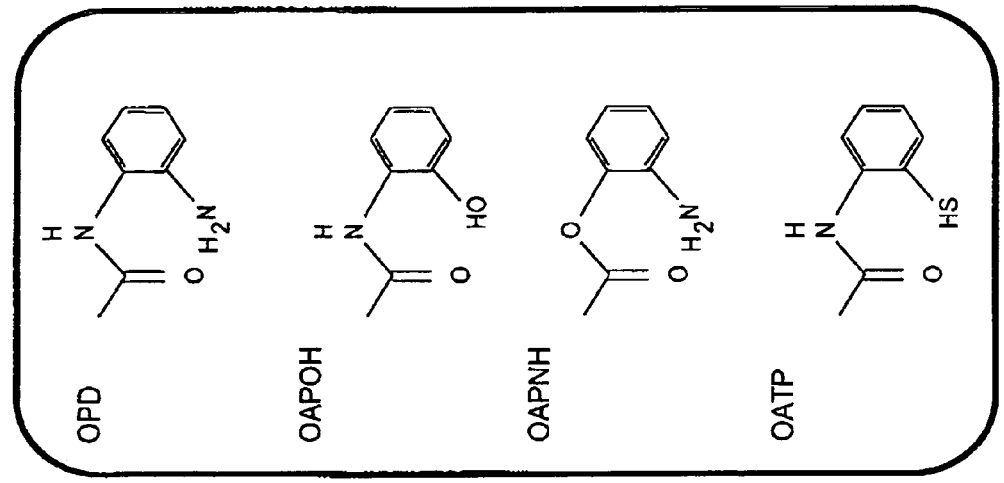
FIG. 5 depicts the structural formulae of o-phenylenediamine (OPD), the amide of o-aminophenol (OAPOH), the ester of o-aminophenol (OAPNH), and o-aminothiophenol (OATP).
Figure 5:
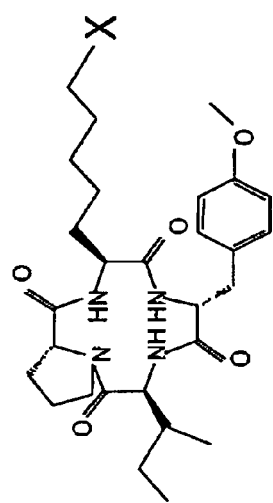

HDAC inhibitory activity in an in vitro system was evaluated for OPD, OAPOH, OAPNH, and OATP. The experimental method followed that of Example 11. Structures of the compounds whose activities were measured are listed in FIG. 5. Inhibitory activity was expressed as the concentration producing 50% inhibition of HDAC activity observed in the negative control ("IC$_{50}$ (µM)") (Table 3).

HDAC inhibitory activity in an in vivo system was measured using p21 promoter induction as index. The experimental method followed that of Example 11. The activity level of the test compounds were compared using the concentration producing 50% of the maximum activity observed in TSA ("EC$_{50}$ (µM)") (Table 3).

TABLE 3

| X | IC$_{50}$(µM) | | | p21 PROMOTER EC$_{50}$(µM) |
|---|---|---|---|---|
| | HDAC1 | HDAC4 | HDAC6 | |
| OPD | 4.04 | 15.7 | 321 | 30.9 |
| OAPOH | 1.22 | 0.23 | 5042 | 55.1 |
| OAPNH | 0.40 | 0.24 | 441 | 12.9 |
| OATP | 2.03 | 0.23 | 408 | >100 |

INDUSTRIAL APPLICABILITY

The compounds of the present invention show strong inhibitory activity against various HDAC subtypes. The compounds of the present invention can be used as pharmaceutical agents for treatment or prevention of diseases associated with HDAC1, 4, and 6. Using the methods for producing the compounds of the present invention, various types of these compounds can be synthesized simply and conveniently. Therefore, using the production methods of the present invention, the structure of the tetrapeptide skeleton can be changed into various forms, and the selectivities of the compounds toward target enzymes can be easily modified. Thus, the methods for producing the compounds of the present invention are expected to contribute to the development of HDAC inhibitors having novel characteristics and the like.

The invention claimed is:

1. A compound represented by formula (1)

<img>Formula (1): macrocyclic structure with R43, R42, R41, R11, R31, R21, R33, R32, R22, R23 substituents and (CH2)n-X chain</img> wherein
$R_{11}$, $R_{21}$, $R_{31}$, and $R_{41}$ independently are a hydrogen or methyl group;

$R_{22}$, $R_{23}$, $R_{32}$, $R_{33}$, $R_{42}$, and $R_{43}$ independently are any one of hydrogen, a linear alkyl group comprising 1 to 6 carbons, a linear alkyl group comprising 1 to 6 carbons to which a non-aromatic cyclic alkyl group or a substituted or unsubstituted aromatic ring is attached, a non-aromatic cyclic alkyl group, or a non-aromatic cyclic alkyl group to which a non-aromatic cyclic alkyl group or a substituted or unsubstituted aromatic ring is attached;

each of $R_{21}$ and $R_{22}$, $R_{31}$ and $R_{32}$, and $R_{41}$ and $R_{42}$ independently form a non-cyclic structure without bonding to each other, or come together to form a cyclic structure by bonding to each other through a linear alkylene group having a chain length of 2 to 5 carbons, a linear alkylene chain having a chain length of 2 to 5 carbons and having attached thereto a branched chain of 3 to 6 carbon atoms, or a linear alkylene chain having a chain length of 2 to 5 carbons and having attached thereto a cyclic structure of 1 to 6 carbon atoms;

n is an integer from 4 to 6; and

X is selected from the group consisting of:

<img>Structures for X: formyl hydroxamic acid, methyl ester carbonyl, trifluoromethyl ketone (F3C), difluoromethyl ketone (F2C), trifluoromethylthiomethyl ketone (CF3-S), 2-aminoanilide, 2-hydroxyanilide, 2-aminophenyl ketone, and 2-mercaptoanilide</img>

2. A histone deacetylase inhibitor comprising the compound of claim 1 as an active ingredient.

3. A tubulin deacetylase inhibitor comprising the compound of claim 1 as an active ingredient.

4. An apoptosis inducer comprising the compound of claim 1 as an active ingredient.

5. A differentiation inducer comprising the compound of claim 1 as an active ingredient.

6. An angiogenesis inhibitor comprising the compound of claim 1 as an active ingredient.

7. A cancer metastasis inhibitor comprising the compound of claim 1 as an active ingredient.

8. A pharmaceutical agent which comprises the compound of claim 1 as an active ingredient.

9. A method for producing the compound of claim 1, wherein the method comprises reacting a compound represented by formula (2)

<img>Formula (2): P1-NR11-CH((CH2)n-X)-COOH</img>

(wherein n, $R_{11}$, and X are as defined in claim 1, and $P_1$ represents an amino protecting group) with a compound represented by formula (3)

<img>Formula (3): HNR21-C(R22)(R23)-CONR31-C(R32)(R33)-CONR41-C(R42)(R43)-COOP2</img>

(wherein $R_{11}$, $R_{21}$, $R_{22}$, $R_{23}$, $R_{31}$, $R_{32}$, $R_{33}$, $R_{41}$, $R_{42}$, and $R_{43}$ are as defined in formula (1) of claim 1, and $P_2$ represents a carboxyl protecting group) in the presence of a peptide coupling agent to yield a compound represented by formula (4)

<img>Formula (4): P1-NR11-CH((CH2)n-X)-CONR21-C(R22)(R23)-CONR31-C(R32)(R33)-CONR41-C(R42)(R43)-COOP2</img>

(wherein n, $R_{11}$, $R_{21}$, $R_{22}$, $R_{23}$, $R_{31}$, $R_{32}$, $R_{33}$, $R_{41}$, $R_{42}$, $R_{43}$, $P_1$, $P_2$, and X are defined above), then subjecting the compound represented by formula (4) to catalytic hydrogenation, acid treatment, or hydrolysis to remove $P_1$ and $P_2$, and subsequently, carrying out a cyclization reaction in the presence of a peptide coupling agent;

reacting a compound represented by formula (5)

<img>Formula (5): P1-NR21-C(R22)(R23)-CONR31-C(R32)(R33)-CONR41-C(R42)(R43)-COOH</img>

(wherein $R_{21}$, $R_{22}$, $R_{23}$, $R_{31}$, $R_{32}$, $R_{33}$, $R_{41}$, $R_{42}$, $R_{43}$, and $P_1$ are as defined above) with a compound represented by formula (6)

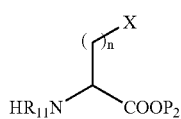 (6)

(wherein n, $R_{11}$, $P_2$, and X are as defined above) in the presence of a peptide coupling agent to yield a compound represented by formula (7)

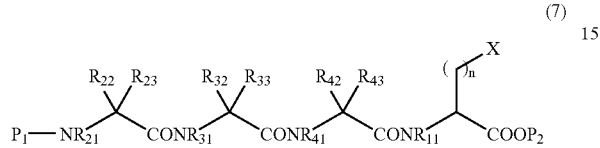 (7)

(wherein n, $R_{11}$, $R_{21}$, $R_{22}$, $R_{23}$, $R_{31}$, $R_{32}$, $R_{33}$, $R_{41}$, $R_{42}$, $R_{43}$, $P_1$, $P_2$, and X are as defined above), then subjecting the compound represented by formula (7) to catalytic hydrogenation, acid treatment, fluoride anion treatment, or hydrolysis to remove $P_1$ and $P_2$, and subsequently, carrying out a cyclization reaction in the presence of a peptide coupling agent; or reacting a compound in which X of the cyclic tetrapeptide of formula (1) is a carboxyl group or a sulfhydryl group individually with trifluoroacetic anhydride, pentafluoropropanoic anhydride, or 1,1,1-trifluoro-3-bromoacetone to change substituent X into a different type of substituent.

* * * * *

UNITED STATES PATENT AND TRADEMARK OFFICE
CERTIFICATE OF CORRECTION

PATENT NO. : 7,662,778 B2
APPLICATION NO. : 10/561298
DATED : February 16, 2010
INVENTOR(S) : Yoshida et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 784 days.

Signed and Sealed this

Thirtieth Day of November, 2010

David J. Kappos
*Director of the United States Patent and Trademark Office*